United States Patent
Evans et al.

(10) Patent No.: US 7,655,795 B2
(45) Date of Patent: Feb. 2, 2010

(54) PROCESS FOR PREPARING PYRROLO[3,2-D]PYRIMIDINE INHIBITORS OF NUCLEOSIDE PHOSPHORYLASES AND NUCLEOSIDASES

(75) Inventors: Gary Brian Evans, Normandale (NZ); Peter Charles Tyler, Northland (NZ)

(73) Assignee: Industrial Research Limited, Auckland (NZ)

( * ) Notice: Subject to any disclaimer, the term of this patent is extended or adjusted under 35 U.S.C. 154(b) by 168 days.

(21) Appl. No.: 10/543,380

(22) PCT Filed: Jan. 30, 2004

(86) PCT No.: PCT/NZ2004/000017

§ 371 (c)(1),
(2), (4) Date: Mar. 22, 2006

(87) PCT Pub. No.: WO2004/069856

PCT Pub. Date: Aug. 19, 2004

(65) Prior Publication Data

US 2006/0217551 A1    Sep. 28, 2006

(30) Foreign Application Priority Data

Feb. 4, 2003    (NZ) .................................. 523970

(51) Int. Cl.
  *C07D 487/04*    (2006.01)
  *A61K 31/519*    (2006.01)
  *A61P 35/02*    (2006.01)
  *A61P 33/02*    (2006.01)
  *C07D 471/04*    (2006.01)
  *A61K 31/4355*    (2006.01)

(52) U.S. Cl. .................... 544/280; 514/265.1; 514/300; 546/118; 546/113

(58) Field of Classification Search ................. 544/280; 514/260.1, 265.1
See application file for complete search history.

(56) References Cited

U.S. PATENT DOCUMENTS

| | | | |
|---|---|---|---|
| 5,985,848 A | 11/1999 | Furneaux et al. |
| 6,066,722 A | 5/2000 | Furneaux et al. |
| 6,228,847 B1 | 5/2001 | Furneaux et al. |
| 6,379,911 B2 | 4/2002 | Schramm et al. |
| 6,458,799 B1 | 10/2002 | Montgomery et al. |
| 6,492,347 B2 | 12/2002 | Furneaux et al. |
| 6,693,193 B1 | 2/2004 | Furneaux et al. |
| 6,764,829 B2 | 7/2004 | Schramm et al. |
| 6,803,455 B2 | 10/2004 | Furneaux et al. |
| 7,022,852 B2 | 4/2006 | Furneaux et al. |
| 7,098,334 B2 | 8/2006 | Furneaux et al. |
| 7,109,331 B2 | 9/2006 | Furneaux et al. |
| 7,211,653 B2 | 5/2007 | Furneaux et al. |
| 7,211,677 B2 | 5/2007 | Furneaux et al. |

2006/0160765 A1    7/2006    Evans et al.

FOREIGN PATENT DOCUMENTS

| | | |
|---|---|---|
| WO | WO 2005/118532 | 12/2005 |
| WO | WO 2006/014913 A2 | 2/2006 |
| WO | WO 2006/123953 A1 | 11/2006 |
| WO | WO 2007/069923 A1 | 6/2007 |
| WO | WO 2007/097647 A1 | 8/2007 |
| WO | WO 2007/097648 A1 | 8/2007 |

OTHER PUBLICATIONS

Karlsson S et al., entitled "Synthesis of enantiomerically pure 4-substituted pyrrolidin-3-ols via asymmetric 1,3-dipolar cycloaddition," Tetrahedron: Asymmetry 12 (2001) 1977-1982.

Filichev V V et al., entitled "Synthesis of 1'-aza-C-nucleosides from (3R,4R)-4-(hydroxymethyl)pyrrolidin-3-ol," Tetrahedron 57 (2001) 9163-9168.

Kamath V P et al., entitled "Synthesis of a potent transition-state inhibitor of 5'-Deoxy-5'-methylthioadenosine phosphorylase," J. Med. Chem. 2004, 47, 1322-1324.

Lewandowicz A et al., entitled "Over-the barrier transition state analoques and crystal structure with Mycobacterium tubersulosis purine nucleoside phosphorylase," Biochemistry 2003, 42, 6057-6066.

Evans G B et al., entitled "Exploring structure-activity relationships of transition state analogues of human purine nucleoside phosphorylase," J. Med. Chem. 2003, 46, 3412-3423.

Wolff M E, entitled "Burger's Medicinal Chemistry and Drug Discovery," Fifth Edition, vol. 1: Principles and Practice, John Wiley & Sons, 1995, 975-977.

Banker G S et al., entitled "Modern Pharmaceutics," Marcel Dekker Inc., Third Edition, Revised and Expanded, 1996, pp. 451 & 596.

"Biocryst Pharmaceuticals, Inc. Announces Preliminary Phase II Trial Data for a Topical Ointment formulation of PNP Drug Drug Candidate, BCX-34" Biocryst News, Apr. 29, 1998.

International Searching Authority, "Written Opinion of the International Searching Authority," for International Application No. PCT/NZ2004/000017, 3 pages, Date of mailing: May 7, 2004.

(Continued)

Primary Examiner—Susanna Moore
(74) Attorney, Agent, or Firm—Amster, Rothstein & Ebenstein LLP

(57) ABSTRACT

The present invention relates to a new process for the preparation of compounds of general formula (I) which are inhibitors of purine nucleoside phosphorylases (PNP), purine phosphoribosyltransferases (PPRT), 5'-methylthioadenosine phosphorylases (MTAP), 5'-methylthioadenosine nucleosidases (MTAN) and/or nucleoside hydrolases (NH). The present invention relates to a new process for the preparation of compounds of general formula (I) which are inhibitors of purine nucleoside phosphorylases (PNP), purine phosphoribosyltransferases (PPRT), 5'-methylthioadenosine phosphorylases (MTAP), 5'-methylthioadenosine nucleosidases (MTAN) and/or nucleoside hydrolases (NH).

18 Claims, No Drawings

OTHER PUBLICATIONS

"International Preliminary Report on Patentability," for International Application No. PCT/NZ2004/000017, 3 pages, Date of completion: Jan. 18, 2005.

Evans G B et al. "Synthesis of a transition state analogue inhibitor of purine nucleoside phosphorylase via the Mannich reaction," Organic Letters 2003, 5(20), 3639-3640.

Modnikova et al., Pyrrolo[3,2-d]pyrimidines. III. 7-Aminomethyl-substituted pyrrolo [3,2-d]pyrimidines, Khimiko-Farmasevticheskii Zjurnal, vol. 16, 1982, pp. 548-552.

Supplementary European Search Report dated May 27, 2009 from the European Patent Office in connection with European Patent Application No. 04706902.6, 2 pages.

Brakta M et al, entitled "Efficient Synthesis of 3H,5H-Pyrrolo[3,2-d] pyrimidin-4-one," J. Chem. Soc. Perkin Trans., 1992, vol. 1, pp. 1883-1884.

Galeazzi, R et al., "Chiral 3-hydroxypyrrolidin-2-ones from a Baylis-Hillman adduct: convergent, stereoselective synthesis of glycosidase inhibitor," Tetrahedron: Asymmetry, vol. 15, pp. 3249-3256, 2004.

Kametani, T et al, "Studies on the Syntheses of Heterocylic Compounds. 762. Synthesis of 3-benzyl-6-methyl-2-oxo-3,6-diazabicyclo[3.1.0]hexane as a synthetic intermediate of mitomycins," Tetrahedron, 1979, 35(3), pp. 313-316.

Lewandowicz A et al. "Energetic Mapping of Transition State Analogue Internations with Human and Plasmodium falciparum Purine Nucleotide Phosphorylases" Journal of Biological Chemistry, 2005, 280(34), 30320-30328.

Lim M-I et al., entitled "A New Synthesis of Pyrrolo[3,2-d]pyrimidines ("9-Deazapurines") via 3-Amino-2-carboalkoxypyrroles," J. Org. Chem., 1979, vol. 44, No. 22, pp. 3826-3829.

STN FILE CA abstract No. 91-123648 (4 pages), downloaded, Jan. 4, 2006.

Miles R W et al., entitled "One-Third-the-Sites Transition-State Inhibitors for Purine Nucleoside Phosphorylase," Biochemistry, 1998, vol. 37, No. 24, pp. 6-12.

Taylor E C et al., entitled "An Expeditious Synthesis of 2-Amino-4(3H)-oxo-5H-pyrrolo[3,2-d] pyrimidine (9-Deazaguanine)," Tetrahedron Letters, 1993, vol. 34, No. 29, pp. 4595-4598.

PROCESS FOR PREPARING PYRROLO[3,2-D]PYRIMIDINE INHIBITORS OF NUCLEOSIDE PHOSPHORYLASES AND NUCLEOSIDASES

This application is a U.S. National Phase of PCT Application No. PCT/NZ2004/000017, filed Jan. 30, 2004 and claims priority to New Zealand Application No. 523970, filed Feb. 4, 2003.

TECHNICAL FIELD

This invention relates to a process for the preparation of certain nucleoside analogues. In particular, the invention relates to a process that includes the reaction of formaldehyde, or a formaldehyde equivalent, with a cyclic amine and a heteroaromatic compound to give methylene linked cyclic amine deazapurines.

BACKGROUND

Nucleoside analogues that are potent inhibitors of purine nucleoside phosphorylase (PNP) and purine phosphoribosyltransferases (PPRT) are useful in treating parasitic infections, T-cell malignancies, autoimmune diseases and inflammatory disorders {see e.g. V. L. Schramm, Biochimica et Biophysica Acta, 1587 (2002) 107-117}. The analogues are also useful for immunosupression in organ transplantation.

Related nucleoside analogues that are potent inhibitors of 5'-methylthioadenosine phosphorylase (MTAP) and 5'-methylthioadenosine nucleosidase (MTAN) are useful:
(a) as anti-microbial compounds, and in decreasing the virulence of microbial infections by decreasing production of the quorum sensing pathway;
(b) as agents for treating parasitic infections such as malaria that infects red blood cells {see e.g. G. A. Kicska et al., J. Biol. Chem., 277 (2002) 3226-3231}; and
(c) as anti-tumour compounds, potentially in combination therapy with methotrexate or azaserine.

The applicants have previously disclosed potent inhibitors of such enzymes in a class called the Immucillins, based upon deazapurines covalently linked directly to aza-sugar moieties (U.S. Pat. Nos. 5,985,848 and 6,066,722, "Inhibitors of Nucleoside Metabolism"; and WO 02/19371, "Nucleoside Metabolism Inhibitors").

In the search for new and improved nucleoside analogues that are potent inhibitors of the aforementioned nucleoside phosphorylases and nucleosidases, the applicants have also discovered a new class of compounds that are potent inhibitors of these nucleoside phosphorylases and hydrolases (PCT Patent Application PCT/NZ03/00186, "Inhibitors of Nucleoside Phosphorylases and Nucleosidases").

The preparation of such nucleoside analogues is by way of multi-step chemical syntheses. Consequently, the time and cost required for each synthesis can be considerable. There is therefore a need for more efficient and cost effective methods of preparing compounds in this new class.

The Mannich reaction is a condensation reaction between three components, namely an amine, formaldehyde and a compound with an active hydrogen atom such as a heteroaromatic compound e.g. indole (pages 812-814, *Vogel's Textbook of Practical Organic Chemistry*, 4th Edition, revised by B. S. Furniss, A. J. Hannaford, V. Rogers, P. W. G. Smith and A. R. Tatchell, Longmans, London, 1978).

Mannich reactions have been used to assemble compounds that incorporate a 9-deazapurine moiety linked via a methylene group to aliphatic and alicyclic amines [G. A. Modnikova et al., "Pyrrolo[3,2-d]pyrimidines. III. 7-Aminomethyl-substituted pyrrolo[3,2-d]pyrimidines", Khim.-farm. Zh., 1983, 352-356 (English translation)]. Compounds that incorporate a pyrimidine moiety linked via a methylene group to a cyclic secondary amine have also been assembled using Mannich reactions. [V. V. Filichev and E. B. Pedersen, "Synthesis of 1'-aza-C-nucleosides from (3R,4R)-4-(hydroxymethyl)pyrrolidin-3-ol", Tetrahedron, 57 (2001) 9163-9168].

The applicants have now found that a Mannich reaction can be used to prepare compounds that incorporate a 9-deazapurine or an 8-aza-9-deazapurine moiety (or their 2-aza-analogues) linked via a methylene group to a cyclic secondary amine. These compounds are described as potent inhibitors, or potentially potent inhibitors, of nucleoside phosphorylases and nucleosidases in PCT Patent Application PCT/NZ03/00186.

It is therefore an object of the present invention to provide a process for preparing these compounds, or at least to provide a useful choice.

STATEMENTS OF INVENTION

In a first aspect, the invention provides process for preparing a compound of the formula (I)

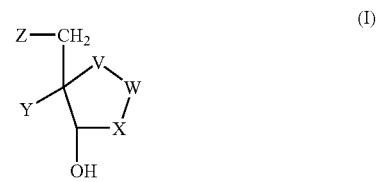

wherein:
V is selected from $CH_2$ and NH, and W is $NR^1$; or
V is $NR^1$, and W is selected from $CH_2$ and NH;
X is selected from $CH_2$ and CHOH in the R or S-configuration, except where W is selected from NH and $NR^1$, then X is $CH_2$;
Y is selected from hydrogen, halogen and hydroxy, except where V is selected from NH and $NR^1$, then Y is hydrogen;
Z is selected from hydrogen, halogen, hydroxy, a sulfonate leaving group, SQ, OQ and Q, where Q is an optionally substituted alkyl, aralkyl or aryl group; and
$R^1$ is a radical of the formula (II)

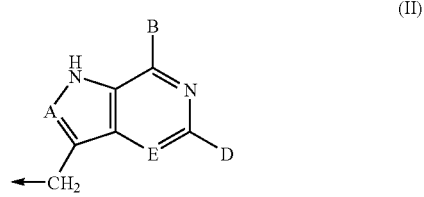

wherein:
A is selected from N, CH and $CR^2$, where $R^2$ is selected from halogen, optionally substituted alkyl, aralkyl or aryl, OH, $NH_2$, $NHR^3$, $NR^3R^4$ and $SR^5$, where $R^3$, $R^4$ and $R^5$ are each optionally substituted alkyl, aralkyl or aryl groups;
B is selected from OH, $NH_2$, $NHR^6$, SH, hydrogen and halogen, where $R^6$ is an optionally substituted alkyl, aralkyl or aryl group;

D is selected from OH, NH$_2$, NHR$^7$, hydrogen, halogen and SCH$_3$, where R$^7$ is an optionally substituted alkyl, aralkyl or aryl group; and E is selected from N and CH;

including reacting a compound of the formula (III)

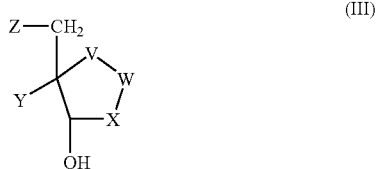

(III)

wherein:

V is selected from CH$_2$ and NH, and W is NH; or

V is NH, and W is selected from CH$_2$ and NH;

X is selected from CH$_2$ and CHOH in the R or S-configuration, except where W is NH, then X is CH$_2$;

Y is selected from hydrogen, halogen and hydroxy, except where V is selected from NH, then Y is hydrogen; and Z is selected from hydrogen, halogen, hydroxy, a sulfonate leaving group, SQ, OQ and Q, where Q is an optionally substituted alkyl, aralkyl or aryl group;

with a compound of the formula (IV)

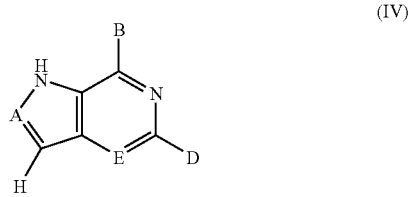

(IV)

wherein A, B, D, and E are as defined above;

and with formaldehyde or a formaldehyde equivalent.

Preferably, Z is hydrogen, halogen, hydroxy, SQ or OQ, where Q is an optionally substituted alkyl, aralkyl or aryl group. It is also preferred that A is CH. It is further preferred that Y is H.

Preferably W is NR$^1$, V is CH$_2$ and X is CH$_2$. It is also preferred that R$^1$ is a radical of formula (II) as defined in claim 1, where A is CH and E is N.

It is further preferred that D is H or NH$_2$. Additionally, it is preferred that B is NH$_2$, OH or Cl.

Preferred processes of the invention include those where Z in the compound of formula (I) is methanesulfonate, p-toluenesulfonate or trifluoromethanesulfonate. Most preferably Z is methanesulfonate.

Preferred processes of the invention also include those where the compounds of formula (III) and (IV) are reacted with formaldehyde. Alternatively it is preferred that the compounds of formula (III) and (IV) are reacted with a formaldehyde equivalent such as paraformaldehyde.

The more preferred processes of the invention include those where the compound of formula (I) is:

(3R,4R)-1-[(9-deazahypoxanthin-9-yl)methyl]-3-hydroxy-4-hydroxymethyl-pyrrolidine;

(3R,4R)-1-[(9-deaza-adenin-9-yl)methyl]-3-hydroxy-4-(hydroxymethyl)-pyrrolidine;

(3R,4S)-4-(benzylthiomethyl)1-[(9-deaza-adenin-9-yl)methyl]-3-hydroxy-pyrrolidine;

(3R,4S)-4-(4-chlorophenylthiomethyl)1-[(9-deaza-adenin-9-yl)methyl]-3-hydroxy-pyrrolidine;

(3R,4R)-1-[(6-chloro-9-deazapurin-9-yl)methyl]-3-hydroxy-4-(hydroxymethyl)-pyrrolidine (3R,4R)-1-[(9-deaza-adenin-9-yl)methyl]-3-hydroxy-4-(methanesulfonyl)-pyrrolidine;

(3R,4S)-1-[(9-deaza-adenin-9-yl)methyl]-3-hydroxy-4-(methylthiomethyl)-pyrrolidine;

(3R,4S)-4-(ethylthiomethyl)-1-[(9-deaza-adenin-9-yl)methyl]-3-hydroxy-pyrrolidine;

(3R,4S)-1-[(9-deaza-adenin-9-yl)methyl]-3-hydroxy-4-(propylthiomethyl)-pyrrolidine;

(3R,4S)-1-[(9-deaza-adenin-9-yl)methyl]-3-hydroxy-4-(isopropylthiomethyl)-pyrrolidine;

(3R,4S)-4-(butylthiomethyl)-1-[(9-deaza-adenin-9-yl)methyl]-3-hydroxy-pyrrolidine;

(3R,4S)-1-[(9-deaza-adenin-9-yl)methyl]-3-hydroxy-4-(phenylthiomethyl)-pyrrolidine;

(3R,4S)-1-[(9-deaza-adenin-9-yl)methyl]-4-(4-fluorophenylthiomethyl)-3-hydroxy-pyrrolidine;

(3R,4S)-4-(3-chlorophenylthiomethyl)-1-[(9-deaza-adenin-9-yl)methyl]-3-hydroxy-pyrrolidine;

(3R,4S)-1-[(9-deaza-adenin-9-yl)methyl]-3-hydroxy-4-(cyclohexylthiomethyl)pyrrolidine;

(3R,4S)-1-[(9-deaza-adenin-9-yl)methyl]-3-hydroxy-4-(4-pyridylthiomethyl)-pyrrolidine;

(3R,4R)-1-[(9-deaza-adenin-9-yl)methyl]-3-hydroxy-(methoxymethyl)-pyrrolidine;

(3R,4R)-4-(benzyloxymethyl)-1-[(9-deaza-adenin-9-yl)methyl]-3-hydroxy-pyrrolidine;

(3R,4R)-1-[(9-deazaguanin-9-yl)methyl]-3-hydroxy-4-hydroxymethyl-pyrrolidine;

(3R,4S)-1-[(9-deazahypoxanthin-9-yl]-3-hydroxy-4-(propylthiomethyl)-pyrrolidine;

(3R,4S)-4-(butylthiomethyl)-1-[(9-deazahypoxanthin-9-yl)methyl]-3-hydroxy-pyrrolidine;

(3R,4S)-1-[(9-deaza-6chloro-purin-9-yl)methyl]-3-hydroxy-4-(2-phenylethyl)pyrrolidine;

(3R,4S)-1-[(9-deazaadenin-9-yl)methyl]-3-hydroxy-4-propyl-pyrrolidine;

(3R,4S)-1-[(9-deazahypoxanthin-9-yl)methyl]-3-hydroxy-4-propyl-pyrrolidine; or (3R,4S)-1-[(9-deazahypoxanthin-9-yl)methyl]-3-hydroxy-4-(methylthiomethyl)-pyrrolidine.

The invention also provides compound of formula (I) when prepared by a process according to claim 1.

In one embodiment, the invention provides a process for preparing a compound of formula (I) as defined in claim 1 including:

(i) reacting a compound of formula (III) as defined in claim 1 with a compound of formula (IV) as defined in claim 1 and with formaldehyde or a formaldehyde equivalent, where any one or more of V, W, X, Y and Z of the compound of formula (III) is protected with a suitable protecting group; and (ii) removing the one or more protecting groups to give the compound of formula (I).

In another embodiment, the invention provides a process for preparing a compound of formula (I) as defined in claim 1 including:

(i) reacting a compound of formula (III) as defined in claim 1 with a compound of formula (IV) as defined in claim 1 and with formaldehyde or a formaldehyde equivalent, where any one or more of A, B, D and E of the compound of formula (IV) is protected with a suitable protecting group; and (ii) removing the one or more protecting groups to give the compound of formula (I).

In still another embodiment, the invention provides a process of preparing a compound of formula (I) as defined in claim 1 including:

(i) reacting a compound of formula (III) as defined in claim 1 with a compound of formula (IV) as defined in claim 1 and with formaldehyde or a formaldehyde equivalent, where any one or more of V, W, X, Y and Z of the compound of formula (III) is protected with a suitable protecting group and where any one or more of A, B, D and E of the compound of formula (IV) is protected with a suitable protecting group; and (ii) removing the one or more protecting groups to give the compound of formula (I).

DETAILED DESCRIPTION

The present invention provides a useful synthetic route to compounds that are potential inhibitors of PNP, PPRT, MTAN, MTAP and/or nucleoside hydrolases (NH). Such compounds may find use in the treatment of parasitic infections, T-cell malignancies, autoimmune diseases and inflammatory disorders. These compounds may also be used as antimicrobial agents, as antitumour agents, or as agents for treating parasitic infections.

Previous synthetic routes to compounds of formula (I) have been time-consuming and costly. In contrast, the present synthesis is a facile route to this useful class of compounds. The synthetic procedure involves using a Mannich reaction to couple a 9-deazapurine or an 8-aza-9-deazapurine moiety (or their 2-aza-analogues) to a cyclic secondary amine.

The applicants have therefore found that the desired compounds of formula (I) are advantageously prepared in good yield in a one-step synthesis.

It will be appreciated that the representation of a compound of formula (I), where B and/or D is a hydroxy group, is of the enol-type tautomeric form of a corresponding amide, and this will largely exist in the amide form. The use of the enol-type tautomeric representation is simply to allow fewer structural formulae to represent the compounds of the invention.

Similarly, it will be appreciated that the representation of a compound of formula (I), where B and/or D is a thiol group, is of the thioenol-type tautomeric form of a corresponding thioamide, and this will largely exist in the thioamide form. The use of the thioenol-type tautomeric representation is simply to allow fewer structural formulae to represent the compounds of the invention.

As used herein, the term "sulfonate leaving group" means an alkyl or aryl sulfonate such as methanesulfonate or benzenesulfonate, or a substituted form thereof such as bromobenzenesulfonate, trifluoromethanesulfonate or p-toluenesulfonate.

As used herein, the term "protecting group" means a group that selectively protects an organic functional group, temporarily masking the chemistry of that without affecting the functional group. Suitable protecting groups are known to 5 those skilled in the art and are described, for example, in *Protective Groups in Organic Synthesis* (3$^{rd}$ Ed.), T. W. Greene and P. G. M. Wuts, John Wiley & Sons Inc (1999).

Compounds of the formula (III) defined above may be prepared by known methods, as described in PCT Patent Application PCT/NZ03/00186 and the references cited therein. Procedures for the preparation of selected compounds of formula (III) are described herein.

Compounds of formula (IV) defined above may be prepared by known methods. In particular, processes for the preparation of the compounds 3H,5H-pyrrolo[3,2-d]pyrimidin-4-one (9-deazahypoxanthine) and 2-amino-3H,5H-pyrrolo[3,2-d]pyrimidin-4-one (9deazaguanine), compounds 1 and 2 shown below, are described in PCT Patent Application PCT/NZ00/00048, "Process for Preparing Inhibitors of Nucleoside Metabolism and Substrates" and in R. H. Furneaux and P. C. Tyler, J. Org. Chem., 64 (1999) 8411-8412. Further, 9-deazaadenine (3) can be prepared by treatment of 9-deazahypoxanthine (1) with POCl$_3$ and then with ethanolic ammonia.

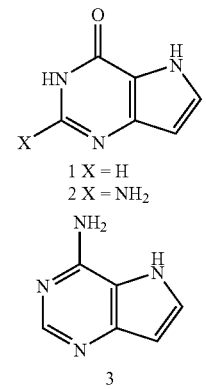

1 X = H
2 X = NH$_2$

3

One advantage of the applicants' new process is that neither the amine nor the heterocyclic component needs to have protecting groups on the functional groups that are not directly involved in the reaction chemistry. Nevertheless, there may be occasions where it is advantageous to utilize a protected form of a compound of formula (III) and/or formula (IV) as components in the reaction.

Suitably protected forms of compounds of formula (III) are described in U.S. Pat. Nos. 5,985,848 and 6,066,722, "Inhibitors of Nucleoside Metabolism" and WO 02/18371, "Nucleoside Metabolism Inhibitors". It is essential that suitably protected forms of compounds of the formula (IV) have a proton at position-9 of the 9-deazapurine or 8-aza-9-deazapurine moiety (or their 2-aza-analogues).

Suitably protected forms of compounds of formula (IV) are described in PCT Patent Application PCT/NZ03/00186, "Inhibitors of Nucleoside Phosphorylases and Nucleosidases". It is essential that protected forms of compounds of the formula (III) have an unprotected ring amino-group.

EXAMPLES

The following examples further illustrate the invention. It is to be appreciated that the invention is not limited to the examples.

Example 1

Mannich Reaction—General Procedure

Scheme 1

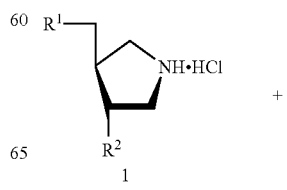

1

+

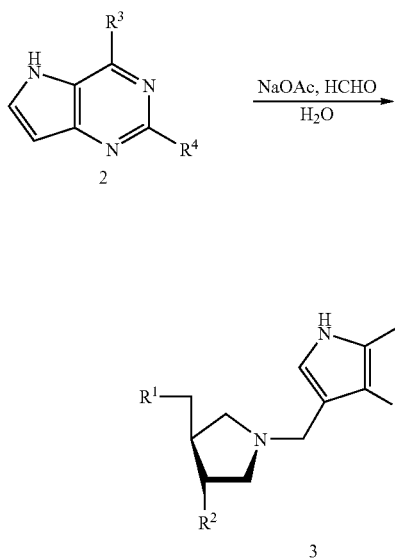

General procedure for the preparation of compounds of formula (3) using the Mannich reaction shown In Scheme 1; Pyrrolidine hydrochlorides of formula (1) (1.0 mol equiv.; as listed in Table 1 as "Amine reactant" unless otherwise specified) and sodium acetate (1.0 mol. equiv.) were dissolved in water and 1,4-dioxane (4:1 v/v, 2 mL per mmol) and to the solution were added aqueous formaldehyde (1.0-1.5 mol. equiv.) and the substituted 9-deazapurine of formula (2) (0.8-1.5 mol equiv.). The reaction was stirred at the temperature and for the time shown in Table 1. Silica gel (1.0 g per mmol of 1) was added and the mixture was evaporated to dryness. Purification by chromatography on silica gel, using gradient elution with $CH_2Cl_2$: MeOH: $NH_4OH$ (95:5:1→80:20:1 v/v/v) as the eluent, afforded the compound of formula (3) as detailed in Table 1 as the free base or partial acetic acid salt, which was converted to the HCl salt by addition and evaporation of excess conc. HCl [Evans, G. B.; Furneaux, R. H.; Tyler, P. C.; Schramm, V. L. *Org. Lett.* 2003, 5, 3639-3640.] The preparations of the pyrrolidine hydrochlorides of formula (1) are exemplified in the Preparative Examples.

TABLE 1

Compounds Prepared via the Mannich Reaction General Procedure

| Cpd No. | Temp (°C.) | Amine reactant | Reaction Time (h) | $R^1$ | $R^2$ | $R^3$ | $R^4$ | Yield (%) |
|---|---|---|---|---|---|---|---|---|
| 4 | 95 | 5 | 16 | OH | OH | OH | H | 47 |
| 6 | 95 | 5 | 1 | OH | OH | $NH_2$ | H | 65 |
| 7 | 95 | 41 | 1 | SBn | OH | $NH_2$ | H | 72 |
| 8 | 95 | 39 | 1 | SPh-p-Cl | OH | $NH_2$ | H | 72 |
| 9 | 95 | 5 | 3 | OH | OH | Cl | H | 78 |
| 10 | 90 | 53 | 1 | $OSO_2Me$ | OH | $NH_2$ | H | 39 |
| 11 | 95 | 32 | 1 | SMe | OH | $NH_2$ | H | 39 |
| 12 | 85 | 33 | 2 | SEt | OH | $NH_2$ | H | 60 |
| 13 | 90 | 34 | 3 | S-n-Pr | OH | $NH_2$ | H | 59 |
| 14 | 95 | 35 | 3 | S-iso-Pr | OH | $NH_2$ | H | 38 |
| 15 | 90 | 36 | 3 | SBu | OH | $NH_2$ | H | 52 |
| 16 | 95 | 37 | 1 | SPh | OH | $NH_2$ | H | 57 |
| 17 | 90 | 38 | 1 | SPh-p-F | OH | $NH_2$ | H | 27 |
| 18 | 90 | 40 | 1.5 | SPh-m-Cl | OH | $NH_2$ | H | 52 |
| 19 | 95 | 44 | 3 | SChx | OH | $NH_2$ | H | 34 |
| 20 | 85 | 45 | 2 | S-4-pyridyl | OH | $NH_2$ | H | 45 |
| 21 | 85 | 42 | 1.5 | OMe | OH | $NH_2$ | H | 59 |
| 22 | 90 | 43 | 1.5 | OBn | OH | $NH_2$ | H | 22 |
| 23 | 95 | 5 | 12 | OH | OH | OH | $NH_2$ | 57 |
| 24 | 90 | 34 | 3 | SPr | OH | OH | H | 78 |
| 25 | 90 | 36 | 3 | SBu | OH | OH | H | 72 |
| 26 | 95 | 49 | 12 | C—Bn | OH | Cl | H | 38 |
| 27 | 95 | 52 | 2.5 | C—Et | OH | $NH_2$ | H | 31 |
| 28 | 95 | 52 | 5 | C—Et | OH | OH | H | 36 |

Example 1.01

(3R,4R)-1-[(9-Deazahypoxanthin-9-yl)methyl]-3-hydroxy-4-hydroxymethyl-pyrrolidine (4). Starting with 9-deazahypoxanthine (Fumeaux and Tyler, *J. Org. Chem.*, 1999, 64, 8411-8412) and (3R,4R)-3-hydroxy-4-hydroxymethyl-pyrrolidine hydrochloride (5) (Evans et al, *J. Med. Chem.*, 2003, 46 5271-5276), the Mannich reaction general procedure (above) was followed to afford compound 4 as the acetic acid salt. After conversion to the HCl salt and $^1$H and $^{13}$C NMR spectra analysis, the compound was found to be identical in all respects with that previously reported (Evans et a.l *J. Med. Chem.* 2003, 46, 5271-5276).

Example 1.02

(3R,4R)-1-[(9-Deaza-adenin-9-yl)methyl]-3-hydroxy-4-(hydroxymethyl)-pyrrolidine (6). Starting with 9-deaza-adenine (Preparative Example 3.01) and (3R,4R)-3-hydroxyhydroxymethyl-pyrrolidine (5), the Mannich reaction general procedure (above) was followed to afford compound 6 as the acetic acid salt. $^1$H NMR (d$_4$-MeOH) δ8.20 (s, 1H), 7.65 (s, 1H), 4.27 (s, 1H), 4.22 (quintet, J=3.0 Hz, 1H), 3.59 (m, 2H), 3.46 (dd, J=11.1, 8.3 Hz, 1H), 3.26 (dd, J=11.4, 5.7 Hz, 1H), 3.11 (dd, J=11.4, 3.0 Hz, 1H), 2.95 (dd, J=11.2, 6.8 Hz, 1H), 2.37 (brs, 1H), 1.82 (s, 3H). $^{13}$C NMR (d$_4$-MeOH) 152.9, 151.9, 147.1, 132.0, 115.8, 108.2, 73.6, 63.1, 61.9, 56.0, 50.8, 49.5, 23.7. HRMS (MH$^+$) calc for $C_{12}H_{18}N_5O_2$: 264.1461. Found 264.1457.

Example 1.03

(3R,4S)-4-Benzylthlomethyl)1-[(9-deaza-adenin-9-yl)methyl]-3-hydroxy-pyrrolidine (7). The Mannich reaction general procedure (above) was followed to afford compound 7 as the acetic acid salt. The acetic acid salt was converted to the free base via ion exchange chromatography. $^1$H NMR (d$_4$-MeOH) 8.17 (s, 1H), 7.46 (s, 1H), 7.26-7.16 (m, 5H), 3.93-3.90 (m, 1H), 3.83-3.74 (m, 2H), 3.68 (s, 2H), 3.03-2.97 (m, 1H), 2.80 (dd, J=10.2, 6.4 Hz, 1H), 2.66-2.58 (m, 2H), 2.38 (dd, J=12.5, 8.9 Hz, 1H), 2.30 (dd, J=9.5, 7.2 Hz, 1H), 2.20-2.14 (m, 1H). $^{13}$C NMR (d$_4$-MeOH) 152.5, 151.4, 147.4, 140.4, 130.4, 130.4, 129.8, 115.5, 112.9, 77.3, 62.7, 59.2, 49.3, 48.6, 37.5, 35.6. HRMS (MH$^+$) calc for $C_{19}H_{24}N_5OS$: 370.1702. Found 370.1694.

Example 1.04

(3R,4S)-4-(4Chlorophenylthlomethyl)1-[(9-deaza-adenin-9-yl)methyl]-3-hydroxy-pyrrolidine (8). The Mannich reaction general procedure (above) was followed to afford compound 8 as the acetic acid salt. $^1$H NMR (d$_4$-MeOH) 8.25 (s, 1H), 7.84 (s, 1H), 7.35-7.23 (m, 5H), 4.54 (s, 2H), 4.30 (m, 1H), 3.74 (dd, J=11.9, 7.9 Hz, 1H), 3.59 (dd, J=12.2, 5.6 Hz, 1H), 3.40-3.15 (m, 4H), 2.89 (dd, J=13.5, 9.1 Hz, 1H), 2.47 (brs, 1H), 1.98 (s, 3H). $^{13}$C NMR (d$_4$-MeOH) 153.0, 151.8, 146.1, 135.7, 134.0, 133.2, 132.2, 130.7, 115.7, 105.5, 74.6, 60.4, 57.3, 49.2, 47.7, 36.1, 23.0. HRMS (MH$^+$) calc for $C_{18}H_{21}ClN_5OS$: 390.1155. Found 390.1264.

Example 1.05

(3R,4R)-1-[(6-Chloro-9-deazapurin-9-yl)methyl]-3-hydroxy-4-(hydroxymethyl)-pyrrolidine (9). Starting with 6-chloro-9-deazapurine (K. Imai, *Chem. Pharm. Bull.*, 1964, 12, 1030) and (3R,4R)-3-hydroxy4-hydroxymethyl-pyrrolidine, the Mannich reaction general procedure (above) was followed to afford compound 9 as the acetic acid salt. $^1$H NMR (D$_2$O) 8.34 (s, 1H), 7.98 (s, 1H), 4.48 (s, 2H), 4.31 (m, 1H), 3.68 (dd, J=12.1, 8.3 Hz, 1H), 3.53 (d, J=5.9 Hz, 2H), 3.45 (dd, J=12.6, 5.5 Hz, 1H), 3.32 (dd, J=12.6, 2.5 Hz, 1H), 3.13 (dd, J=12.0, 7.4 Hz, 1H), 2.40 (brs, 1H), 1.82 (s, 3H). $^{13}$C NMR (d$_4$-MeOH) 149.7, 148.6, 143.4, 137.6, 124.8, 104.5, 71.3, 60.7, 59.8, 54.4, 48.0, 47.8, 23.5. HRMS (MH$^+$) calc for $C_{12}H_{16}ClN_4O_2$: 283.0962. Found 283.0973.

Example 1.06

(3R,4R)-1-[(9-Deaza-adenin-9-yl)methyl]-3-hydroxy-4-(methanesulfonyl)-pyrrolidine (10). The Mannich reaction general procedure (above) was followed to afford compound 10. $^1$H NMR (d$_4$-MeOH) 8.17 (s, 1H), 7.52 (s, 1H), 4.30-3.82 (m, 5H), 3.10-3.00 (m, 1H), 3.06 (s, 3H), 2.94 (dd, J=10.3, 6.3 Hz, 1H), 2.71 (dd, J=10.3, 4.1 Hz, 1H), 2.53 (dd, J=10.1, 6.7 Hz, 1H), 2.43-2.34 (m, 1H). $^{13}$C NMR (d$_4$-MeOH) 152.6, 151.5, 147.2, 130.7, 115.6, 112.0, 73.8, 71.8, 62.4, 56.0, 49.4, 49.1, 37.5.

Example 1.07

(3R,4S)-1-[(9-Deaza-adenin-9-yl)methyl]-3-hydroxy-4-(methylthlomethyl)-pyrrolidine (11). The Mannich reaction general procedure (above) was followed to afford compound 11 as the acetic acid salt. After conversion to the HCl salt and $^1$H and $^{13}$C NMR spectra analysis, the compound was found to be identical in all respects with that previously reported. (Evans et al., *J. Med. Chem.* 2003, 46, 5271-5276).

Example 1.08

(3R,4S)-4-(Ethylthiomethyl)-1-[(9-deaza-adenin-9-yl)methyl]-3-hydroxy-pyrrolidine (12). The Mannich reaction general procedure (above) was followed to afford compound 12. $^1$H NMR (d$_4$-MeOH) 8.16 (s, 1H), 7.52 (s, 1H), 4.00-3.82 (m, 3H), 3.12 (dd, J=9.9, 7.9 Hz, 1H), 2.92 (dd, J=10.5, 6.3 Hz, 1H), 2.76-2.68 (m, 2H), 2.55-2.41 (m, 4H), 2.25-2.15 (m, 1H), 1.21 (t, J=7.4 Hz, 3H). $^{13}$C NMR (d$_4$-MeOH) 152.5, 151.5, 147.3, 130.7, 115.6, 112.1, 77.0, 62.4, 59.1, 49.4, 48.8, 35.5, 27.2, 15.5. HRMS (MH$^+$) calc for $C_{14}H_{22}N_5OS$: 308.1540. Found 308.1535.

Example 1.09

(3R,4S)-1-[(9-Deaza-adenin-9-yl)methyl]-3-hydroxy-4-(propylthiomethyl)-pyrrolidine (13). The Mannich reaction general procedure (above) was followed to afford compound 13. $^1$H NMR (d$_4$-MeOH) 8.17 (s, 1H), 7.50 (s, 1H), 4.00-3.79 (m, 3H), 3.08 (dd, J=9.8, 7.9 Hz, 1H), 2.86 (dd, J=10.3, 6.4 Hz, 1H), 2.72-2.62 (m, 2H), 2.50-2.38 (m, 4H), 2.22-2.12 (m, 1H), 1.55 (sextet, J=7.3 Hz, 2H), 0.95 (t, J=7.3 Hz, 3H). $^{13}$C NMR (d$_4$-MeOH) 152.5, 151.4, 147.4, 130.5, 115.6, 112.7, 77.2, 62.6, 59.2, 49.4, 49.0, 36.1, 35.6, 24.3, 14.1. HRMS (MH$^+$) calc for $C_{15}H_{24}N_5OS$: 322.1696. Found 322.1709.

Example 1.10

(3R,4S)-1-[(9-Deaza-adenin-9-yl)methyl]-3-hydroxy-4-(isopropylthiomethyl)-pyrrolidine (14). A variation of the Mannich reaction general procedure (above) using 20% 1,4-dioxane in water as the solvent and 0.9 mol equiv. of 9-deazaadenine afforded the crude title compound 14 (386 mg, 80%) after column chromatography on silica eluting with $CH_2Cl_2$:MeOH:NH$_4$OH (8:1.8:0.2). Residual impurities could be removed by column chromatography on silica eluting with CH$_2$Cl$_2$:NH$_3$ (7N) in MeOH to afford title compound 14 (183 mg, 38%). $^1$H NMR (MeOH-d$_4$): δ ppm: 8.16 (s, 1H), 7.49 (s, 1H), 3.99-3.94 (m, 1H), 3.82 (dd, J=18.7, 13.4 Hz, 1H), 3.04 (dd, J=9.7, 7.9 Hz, 1H), 2.95-2.82 (m, 2H), 2.75 (dd, J=12.5, 6.0 Hz, 1H), 2.66 (dd, J=10.3, 4.2 Hz, 1H), 2.50 (dd, J=12.5, 9.1 Hz, 1H), 2.38 (dd, J=9.7, 7.1 Hz, 1H), 2.21-2.10 (m, 1H), 1.23, 1.22 (2s, 3H each). $^{13}$C NMR (MeOH-d$_4$): δ ppm: 152.48, 151.38, 147.40, 130.45, 115.54, 112.90, 77.29, 62.66, 59.26, 49.32, 49.09, 36.49, 34.66, 24.19.

Example 1.11

(3R,4S)-4-(Butylthiomethyl)-1-[(9-deaza-adenin-9-yl)methyl]-3-hydroxy-pyrrolidine (15). The Mannich reaction general procedure (above) was followed to afford compound 15. $^1$H NMR (d$_4$-MeOH) 8.16 (s, 1H), 7.50 (s, 1H), 3.99-3.79 (m, 3H), 3.08 (dd, J=9.7, 7.9 Hz, 1H), 2.87 (dd, J=10.3, 6.4 Hz, 1H), 2.75-2.69 (m, 2H), 2.51-2.38 (m, 4H), 2.22-2.12 (m, 1H), 1.55-1.32 (m, 4H), 0.90 (t, J=7.3 Hz, 3H). $^{13}$C NMR (d$_4$-MeOH) 152.5, 151.4, 147.4, 130.5, 115.6, 112.6, 77.1, 62.6, 59.2, 49.4, 49.0, 36.1, 33.3, 33.2, 23.3, 14.4. HRMS (MH$^+$) calc for C$_{16}$H$_{26}$N$_5$OS: 336.1853. Found 336.1850.

Example 1.12

(3R,4S)-1-[(9-Deaza-adenin-9-yl)methyl]-3-hydroxy-4-(phenylthiomethyl)-pyrrolidine (16). The Mannich reaction general procedure (above) was followed to afford compound 16. $^1$H NMR (d$_4$-MeOH) 8.22 (s, 1H), 7.74 (s, 1H), 7.33-7.15 (m, 2H), 4.43 (s, 2H), 4.26 (m, 1H), 3.62 (dd, J=11.7, 7.9 Hz, 2H), 3.48 (dd, J=12.0, 5.6 Hz, 1H), 3.25 (t, dd, J=12.0, 3.3 Hz, 1H), 3.15 (m, 2H), 2.85 (dd, J=13.5, 9.1 Hz, 1H), 2.43 (m, 1H). $^{13}$C NMR (d$_4$-MeOH) 152.9, 152.1, 146.8, 136.8, 132.7, 131.4, 130.6, 128.1, 115.8, 106.3, 74.9, 60.6, 57.4, 49.7, 47.7, 36.3. HRMS (MH$^+$) calc for C$_{18}$H$_{25}$N$_5$OS: 356.1545. Found 356.1542.

Example 1.13

(3R,4S)-1-[(9-Deaza-adenin-9-yl)methyl]-4-(4-fluorophenylthiomethyl)-3-hydroxy-pyrrolidine (17). The Mannich reaction general procedure (above) was followed to afford compound 17. $^1$H NMR (d$_4$-MeOH) 8.16 (s, 1H), 7.46 (s, 1H), 7.40-7.30 (m, 2H), 7.00-6.90 (m, 2H), 4.02-3.97 (m, 1H), 3.86-3.75 (m, 2H), 3.11 (dd, J=12.9, 5.9 Hz, 1H), 3.00 (t, J=8.7 Hz, 1H), 2.90-2.75 (m, 2H), 2.65-2.59 (m, 1H), 2.41-2.32 (m, 1H), 2.20-2.10 (m, 1H). $^{13}$C NMR (d$_4$-MeOH) 165.5, 162.0, 152.5, 151.4, 147.4, 134.1, 134.0, 133.1, 130.4, 117.4, 117.1, 115.5, 112.9, 77.2, 62.7, 59.0, 49.3, 48.8, 39.1. HRMS (MH$^+$) calc for C$_{18}$H$_{21}$N$_5$OFS: 374.1445. Found 374.1438.

Example 1.14

(3R,4S)-4-(3-Chlorophenylthiomethyl)-1-[(9-deaza-adenin-9-yl)methyl]-3-hydroxy-pyrrolidine (18). The Mannich reaction general procedure (above) was followed to afford compound 18. $^1$H NMR (d$_4$-MeOH) 8.16 (s, 1H), 7.46 (s, 1H), 7.25-7.05 (m, 4H), 4.01-3.97 (m, 1H), 3.87-3.76 (m, 2H), 3.18 (dd, J=12.9, 5.9 Hz, 1H), 2.99 (dd, J=9.8, 7.9 Hz, 1H), 2.94-2.86 (m, 2H), 2.64 (dd, J=10.2, 4.3 1H), 2.41 (dd, J=9.9, 7.0 Hz, 1H), 2.26-2.15 (m, 1H). $^{13}$C NMR (d$_4$-MeOH) 152.5, 151.4, 147.4, 140.7, 136.1, 131.6, 130.4, 129.8, 128.6, 127.4, 115.5, 112.8, 77.1, 62.6, 58.9, 49.3, 48.7, 37.4. HRMS (MH$^+$) calc for C$_{18}$H$_{21}$N$_5$OClS: 390.1150. Found 390.1142.

Example 1.15

(3R,4S)-1-[(9-Deaza-adenin-9-yl)methyl]-3-hydroxy-4-(cyclohexylthiomethyl)pyrrolidine (19). A variation of the Mannich reaction general procedure (above) using 20% 1,4-dioxane in water as the solvent and 0.9 mol equiv. of 9-deazaadenine afforded the crude title compound 19 (333 mg, 79%) after column chromatography on silica eluting with CH$_2$Cl$_2$:MeOH:NH$_4$OH (8:1.8:0.2 v/v/v). Residual impurities could be removed by column chromatography on silica eluting with CH$_2$Cl$_2$:NH$_3$ (7N) in MeOH (9:1 v/v) to afford title compound 19 (144 mg, 34%). $^1$H NMR (MeOH-d$_4$): δ ppm: 8.15 (s, 1H), 7.50 (s, 1H), 3.97-3.92 (m, 1H), 3.82 (dd, J=19.1, 13.4 Hz, 2H), 3.06-3.00 (m, 1H), 2.84 (dd, J=10.3, 6.4 Hz, 1H), 2.75 (dd, J=12.5, 5.9 Hz, 1H), 2.67-2.58 (m, 2H), 2.48 (dd, J=12.5, 9.3 Hz, 1H), 2.37 (dd, J=9.8, 7.2 Hz, 1H), 2.20-2.08 (m, 1H), 1.94-1.92 (m, 2H), 1.74-1.72 (m, 2H), 1.60-1.58 (m, 1H), 1.36-1.19 (m, 5H). $^{13}$C NMR (MeOH-d$_4$): δ ppm; 152.48, 151.35, 147.32, 130.50, 115.48, 112.74, 77.21, 62.62, 59.18, 49.38, 49.26, 45.10, 35.27, 35.20, 34.18, 27.48, 27.39.

Example 1.16

(3R,4S)-1-[(9-Deaza-adenin-9-yl)methyl]-3-hydroxy(4-pyridylthiomethyl)-pyrrolidine (20). The Mannich reaction general procedure (above) was followed to afford compound 20. $^1$H NMR (D$_2$O) 8.43 (d, J=7.2 Hz, 1H), 8.42 (s, 1H), 8.00 (s, 1H), 7.77 (d, J=7.2 Hz, 1H), 4.64 (s, 2H), 4.52-4.47 (m, 1H), 3.94 (dd, J=12.1, 8.0 Hz, 1H), 3.67 (dd, J=12.6, 5.7 Hz, 1H), 3.50-3.15 (m, 4H), 2.78-2.64 (m, 1H). $^{13}$C NMR (D$_2$O) 163.9, 150.2, 144.6, 139.5, 135.4, 122.8, 113.2, 102.7, 73.0, 59.0, 55.9, 48.1, 44.4, 31.5. HRMS (MH$^+$) calc for C$_{17}$H$_{21}$N$_6$OS: 357.1492. Found 357.1509.

Example 1.17

(3R,4R)-1-[(9-Deaza-adenin-9-yl)methyl]-3-hydroxy-4-(methoxymethyl)-pyrrolidine (21). The Mannich reaction general procedure (above) was followed to afford compound 21. $^1$H NMR (d$_4$-MeOH) 8.19 (s,. 1H), 7.63 (s, 1H), 4.18-4.05 (m, 3H), 3.40-2.28 (m, 3H), 3.30 (s, 3H), 3.10 (dd, J=11.0, 5.7 Hz, 1H), 2.95 (dd, J=11.0, 3.3 Hz, 1H), 2.77 (dd, J=10.8, 6.7 Hz, 1H), 2.41-2.29 (m, 1H). $^{13}$C NMR (d$_4$-MeOH) 152.7, 151.8, 147.2, 131.6, 115.7, 109.5, 74.3, 74.1, 62.2, 59.6, 56.5, 49.4, 49.0. HRMS (MH$^+$) calc for C$_{13}$H$_{20}$N$_5$O$_2$: 278.1612. Found 278.1626.

Example 1.18

(3R,4R)-4-(Benzyloxymethyl)-1-[(9-deaza-adenin-9-yl)methyl]-3-hydroxy-pyrrolidine (22). The Mannich reaction general procedure (above) was followed to afford compound 22. $^1$H NMR (d$_4$-MeOH) 8.17 (s, 1H), 7.55 (s, 1H), 7.30-7.20 (m, 5H), 4.46 (bs, 2H), 4.10-4.00 (m, 3H), 3.55-3.38 (m, 2H), 3.23-3.18 (m, 1H), 2.98 (dd, J=10.7, 5.8 Hz, 1H), 2.85 (dd, J=10.7, 3.4 Hz, 1H), 2.68 (dd, J=10.4, 6.9 Hz, 1H), 2.38-2.30 (m, 1H). $^{13}$C NMR (d$_4$-MeOH) 152.6, 151.7, 147.2, 139.9, 131.3, 129.8, 129.3, 129.1, 115.6, 110.4, 74.5, 74.3, 71.9, 62.3, 56.6, 49.4, 49.0.

Example 1.19

(3R,4R)-1-[(9-Deazaguanin-9-yl)methyl]-3-hydroxy-4-hydroxymethyl-pyrrolidine (23). (3R,4R)-3-Hydroxy-4-hydroxymethyl-pyrrolidine hydrochloride (5) (154 mg, 1.0 mmol) and sodium acetate (82 mg, 1.0 mmol) were dissolved in water (2 mL) and to the solution were added aqueous formaldehyde (82 µL, 1.0 mmol) and 9-deazaguanine (Furneaux and Tyler, *J. Org. Chem.*, 1999, 64, 8411-8412) (120 mg, 0.8 mmol). The reaction was stirred at 95° C. for 12 h. Silica gel (1.0 g) was added and the mixture was evaporated to dryness. Purification by chromatography on silica gel, using $CH_2Cl_2$: MeOH: $NH_4OH$ (5:4:1 v/v/v) as the eluent, afforded title compound 23 as the acetic acid salt. After conversion to the HCl salt and $^1H$ and $^{13}C$ NMR spectra analysis, the compound was found to be identical in all respects with that previously reported (Evans et al., *J. Med. Chem.* 2003, 46, 5271-5276).

Example 1.20

(3R,4S)-1-[(9-Deazahypoxanthin-9-yl]-3-hydroxy-4-(propylthiomethyl)-pyrrolidine (24). The Mannich reaction general procedure (above) was followed to afford compound 24. $^1H$ NMR ($d_4$-MeOH/$D_2O$) 7.99 (s, 1H), 7.53 (s, 1H), 4.06-3.98 (m, 1H), 3.92-3.80 (m, 2H), 3.06 (dd, J=9.8, 8.0 Hz, 1H), 2.90 (dd, J=10.5, 6.5 Hz, 1H), 2.79-2.65 (m, 2H), 2.52-2.38 (m, 4H), 2.22-2.15 (m, 1H), 1.57 (sextet, J=7.3 Hz, 2H), 0.95 (t, J=7.3 Hz, 3H). $^{13}C$ NMR ($d_4$-MeOH) 145.7, 143.7, 131.0, 113.6, 77.0, 62.1, 58.6, 48.9, 48.5, 35.9; 35.6, 24.2, 14.2.

Example 1.21

(3R,4S)-4-(Butylthiomethyl)-1-[(9-deazahypoxanthin-9-yl)methyl]-3-hydroxy-pyrrolidine (25). The Mannich reaction general procedure (above) was followed to afford compound 25. $^1H$ NMR ($d_4$-MeOH/$CDCl_3$) 7.86 (s, 1H), 7.38 (s, 1H), 4.00-3.92 (m, 1H), 3.82-3.75 (m, 2H), 3.07 (dd, J=9.8, 8.0 Hz, 1H), 2.85-2.70 (m, 3H), 2.55-2.42 (m, 3H), 2.37-2.15 (m, 2H), 1.60-1.32 (m, 4H), 0.90 (t, J=7.3 Hz, 3H). $^{13}C$ NMR ($d_4$-MeOH/$D_2O$) 156.6, 145.6, 142.9, 129.9, 119.6, 114.7, 77.4, 63.0, 59.6, 49.4, 49.1, 36.6, 33.6, 33.3, 23.5, 14.9. HRMS (MH$^+$) calc for $C_{16}H_{25}N_4O_2S$: 337.1693. Found 337.1684.

Example 1.22

(3R,4S)-1-[(9-Deaza-6-chloro-purin-9-yl)methyl]-3-hydroxy-4-(2-phenylethyl)pyrrolidine (26). A variation of the Mannich reaction general procedure (above) using 0.9 mol equiv. of 6-chloro-9-deazapurine (K. Imai, *Chem. Pharm. Bull.*, 1964, 12,1030) afforded the title compound 26 (Scheme 2). In comparison to the standard procedure the reaction mixture did not form a solution but a brown slurry which was diluted with 1,4-dioxane before being preabsorbed onto silica gel. Column chromatography eluting with $CH_2Cl_2$: MeOH (4:1 v/v) followed by $CH_2Cl_2$: MeOH: $NH_4OH$ (5:4.5:0.5 v/v/v) gave 26 in 38% yield. $^1H$ NMR (300 MHz, MeOH-$d_4$): δ ppm: 8.71 (s, 1H), 8.12 (s, 1H), 7.17 (s, 5H), 4.55 (s, 1H), 4.18 (m, 1H), 3.56 (m, 2H), 3.31 (m, 1H), 3.04 (dd, J=11.6, 7.7 Hz, 1H), 2.64 (m, 2H), 2.21 (m, 1H), 1.87 (m, 1H), 1.61 (m, 1H). $^{13}C$ NMR (300 MHz, MeOH-$d_4$): δ ppm: 151.62, 151.35, 145.02, 142.99, 138.11, 129.84, 129.82, 127.46, 126.81, 107.73, 75.68, 61.00, 58.48, 49.51, 47.56, 35.26, 34.88.

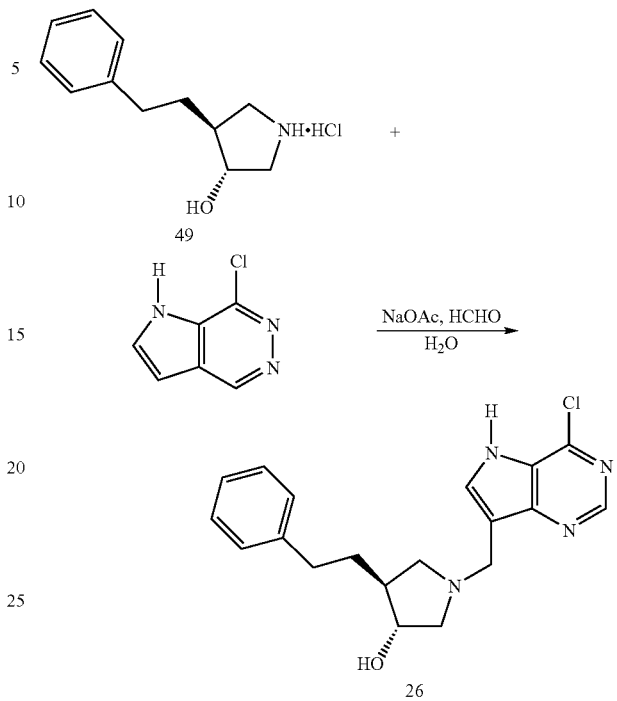

Scheme 2

Example 1.23

(3R,4S)-1-[(9-Deazaadenin-9-yl)methyl]-3-hydroxy-4-propyl-pyrrolidine (27). A variation of the Mannich reaction general procedure (above) using 0.9 mol equiv. of 9-deazaadenine afforded the crude title compound 27 (136 mg, 73%) after column chromatography on silica eluting with $CH_2Cl_2$: MeOH: $NH_4OH$ (8:1.8:0.2 v/v/v). Residual impurities could be removed by column chromatography on silica eluting with MeCN:$NH_4OH$ (4:1 v/v) to give 27 in 31% yield. NMR (300 MHz, MeOH-$d_4$): δ ppm: 8.18 (s, 1H), 7.51 (s, 1H), 3.91-3.85 (m, 3H), 3.10 (dd, J=9.6, 8.0 Hz, 1H), 2.82-2.72 (m, 2H), 2.22 (dd, J=9.6, 8.0 Hz, 1H), 2.04-1.95 (m, 1H), 1.56-1.44 (m, 1H), 1.39-1.21 (m, 3H), 0.92-0.87 (m, 3H). $^{13}C$ NMR (300 MHz, MeOH-$d_4$): δ ppm: 152.52, 151.45, 147.37, 130.59, 115.55, 112.50, 77.94, 62.63, 59.94, 49.55, 48.59, 36.89, 22.67, 14.91.

Example 1.24

(3R,4S)-1-[(9-Deazahypoxanthin-9-yl)methyl]-3-hydroxypropyl-pyrrolidine (28). A variation of the Mannich reaction general procedure (above) using 0.9 mol equiv. of 9-deazahypoxanthine afforded the crude title compound 28 (90 mg, 61%) after column chromatography on silica eluting with $CH_2Cl_2$: MeOH: $NH_4OH$ (5:4.5:0.5 v/v/v). Residual impurities (9-deazahypoxanthine) could be removed by column chromatography on silica eluting with $CH_2Cl_2$:MeOH: $NH_4OH$ (8:1.8:0.2 v/v/v) to give 28 in 36% yield. NMR (300 MHz, MeOH-$d_4$, ~30% $CDCl_3$): δ ppm: 7.86 (s, 1H), 7.39 (s, 1H), 3.89-3.76 (m, 3H), 3.09 (dd, J=9.5, 7.9 Hz, 1H), 2.79-2.69 (m, 2H), 2.18-2.12 (m, 1H), 2.05-1.96 (m, 1H), 1.55-1.46 (m, 1H), 1.41-1.23 (m, 3H), 0.94-0.89 (m, 3H). $^{13}C$ NMR (300 MHz, MeOH-$d_4$, ~30% $CDCl_3$): δ ppm: 145.59, 142.99, 129.93, 114.50, 78.14, 62.95, 60.24, 49.78, 48.94, 37.07, 22.80, 15.29.

Preparative Example 1

Procedures for the Synthesis of (3R,4S)-3-hydroxy-4-(alkyl-, aralkyl-, and aryl-thiomethyl)pyrrolidines.

General Preparative method. 4-Substituted-4-thiopyrrolidines were prepared essentially following the method detailed in Preparative Example 1.01 for compound 32, but with the modifications noted for each Preparative Example and using the appropriate sodium thiolate. In cases when the sodium thiolate was not directly available it was pre-formed by treating a stirred mixture of NaH (2.85 mmol) in DMF (5 mL) at 0° C. with the appropriate thiol (2.85 mmol). After stirring the mixture for 10 min, a solution of the mesylate (450 mg, 1.53 mmol) was added as a solution in DMF (5 mL) and the mixture was stirred at RT until the complete consumption of the mesylate was observed (0.5-4 h) by TLC.

Preparative Example 1.01

(3R,4S)-3-Hydroxy-4-(methylthiomethyl)-pyrrolidine (32), Scheme 3. Methanesulfonyl chloride (0.950 mL, 12.3 mmol) was added to a solution of (3R,4R)-N-tert-butoxycarbonyl-3-hydroxy-4-hydroxymethyl-pyrrolidine (29) (Evans et al., *J. Med. Chem.*, 2003, 46, 5271-5276) (2.16 g, 9.94 mmol) and diisopropylethyl amine (2.65 mL, 15.0 mmol) in DCM (40 mL) cooled to −78° C. over 5 min. After stirring at −78° C. for 40 min, aqueous 2M HCl was added, the organic phase was separated. The aqueous phase was extracted with DCM (×2). The combined organic extract was washed with sat. aqueous $NaHCO_3$ then brine and dried ($MgSO_4$). Normal processing and chromatography gave (1.99 g, 6.74 mmol, 68%) of mesylate 30 as a colourless glass. HRMS (MH$^+$) calc for $C_{11}H_{21}NO_6SNa$: 318.0982. Found 318.0979. A solution of mesylate 30 (450 mg, 1.53 mmol) in DMF (5 mL) was added to a stirred solution of sodium thiomethoxide (200 mg, 2.85 mmol) in DMF (3 mL) and the mixture was stirred for 1 h. Toluene (50 mL) and $H_2O$ (50 mL) were added and shaken, the phases separated, the organic layer dried ($MgSO_4$) and the solvent removed at reduced pressure. The crude product that was purified by chromatography on silica, eluting with 10-50% EtOAc/petroleum ether to afford intermediate 31 (210 mg, 0.849 mmol, 55%). A solution of this material in methanol (3 mL) was treated with cHCl (1 mL). After 1 h, the solution was concentrated to dryness to give title compound 32 as a solid residue (0.830 mmol, 98%). The solid residue was dissolved in $H_2O$ (10 mL) or $D_2O$ (for NMR samples) and the solvent removed (×3). $^1$H NMR ($D_2O$) 4.40 (q, J=3.1 Hz, 1H), 3.67 (dd, J=12.0, 6.6 Hz, 1H), 3.50 (dd, J=12.8, 5.1 Hz, 1H), 3.28 (dd, J=12.8, 3.0 Hz, 1H), 3.22 (dd, J=8.7, 3.4 Hz, 1H), 2.73-2.66 (m, 1H), 2.58-2.50 (m, 2H), 2.40-2.30 (m, 2H) 2.13 (s, 3H). $^{13}$C NMR ($D_2O$) 73.5, 51.5, 48.6, 45.2, 34.3, 14.9.

Scheme 3

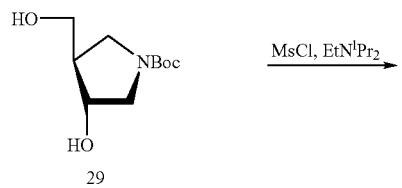

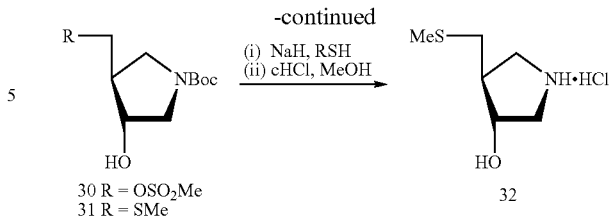

30 R = $OSO_2Me$
31 R = SMe

Preparative Example 1.02

(3R,4S)-4-(Ethylthiomethyl)-3-hydroxy-pyrrolidine (33). Following the general procedure outlined above, mesylate 30 (260 mg, 0.880 mmol) was processed to afford title compound 33 (100 mg, 0.506 mmol, 58%). $^1$H NMR ($D_2O$) 4.30-4.24 (m, 1H), 3.53 (dd, J=12.3, 7.2 Hz, 1H), 3.37 (dd, J=12.8, 5.2 Hz, 1H), 3.14 (dd, J=12.8, 3.1 Hz, 1H), 3.07 (dd, J=12.2, 5.7 Hz, 1H), 2.65-2.55 (m, 1H), 2.46 (q, J=7.4 Hz, 2H), 2.40-2.30 (m, 2H) 1.09 (t, J=7.4 Hz, 3H). $^{13}$C NMR ($D_2O$) 73.6, 51.5, 48.6, 45.6, 31.7, 26.0, 14.4. HRMS (MH$^+$) calc for $C_7H_{16}NOS$: 162.0947. Found 162.0952.

Preparative Example 1.03

(3R,4S)-3-Hydroxy-4-(propylthiomethyl)-pyrrolidine (34). Following the general procedure outlined above, mesylate 30 (264 mg, 0.894 mmol) was processed to afford 34 (139 mg, 0.656 mmol, 73%). $^1$H NMR ($D_2O$) 4.41-4.37 (m, 1H), 3.67 (dd, J=12.3, 7.2 Hz, 1H), 3.50 (dd, J=12.8, 5.2 Hz, 1H), 3.27 (dd, J=12.8, 3.1 Hz, 1H), 3.21 (dd, J=12.2, 5.6 Hz, 1H), 2.76-2.71 (m, 1H), 2.61-2.50 (m, 4H), 1.59 (sextet, J=7.3 Hz), 0.95 (t, J=7.3 Hz, 3H). $^{13}$C NMR ($D_2O$) 73.6, 51.5, 48.6, 45.7, 34.1, 32.1, 22.7, 13.1. HRMS (MH$^+$) calc for $C_8H_{18}NOS$: 176.1104. Found 176.1106.

Preparative Example 1.04

(3R,4S)-3-Hydroxy-4-(isopropylthiomethyl)-pyrrolidine hydrochloride (35). To a solution of 2-propanethiol (0.36 mL, 3.9 mmol) in DMF (10 mL) at 0° C. was added 60% NaH (145 mg, 3.6 mmol). After 10 min. of stirring a solution of the mesylate 30 (565 mg, 1.91 mmol) in DMF (10 mL) was added. Stirring was continued while the reaction was allowed to attain r.t. After completion, the reaction was quenched with aq. $NaHCO_3$, toluene was added and the reaction was processed normally to give the crude intermediate which was subjected to column chromatography on silica eluting with petroleum ether EtOAc (4:1→1:1 v/v) to give the clean intermediate (3R,4S)-N-tert-butoxycarbonyl-3-hydroxy-4-(isopropylthiomethyl)-pyrrolidine as a colourless syrup (490 mg, 97%). NMR (300 MHz, $CDCl_3$): δ ppm: 4.18-4.11 (m, 1H), 3.72-3.60 (m, 2H), 3.28-3.18 (m, 1H), 3.13 (dd, J=11.1, 6.7 Hz, 1H), 2.95 (sept., J=6.7 Hz, 1H), 2.69-2.50 (m, 2H), 2.33-2.22 (m, 1H), 1.46 (s, 9H), 1.29, 1.27 (s, 3H each). $^{13}$C NMR (300 MHz, $CDCl_3$): δ ppm: (note that some peaks are doubled due to slow conversion of rotamers) 154.93, 79.97, (75.48, 74.64), (52.81, 52.55), (49.69, 49.42), (46.13, 45.35), 35.71, 32.32, 28.87, 23.73, 23.69. A solution of this material in MeOH (10 mL) was treated with 12 N (conc.) HCl (4 mL) at 40° C. for 30 min. to give the crude title compound 35 which was used directly in a Mannich-type reaction.

Preparative Example 1.05

(3R,4S)-4-(Butylthiomethyl)-3-hydroxy-pyrrolidine (36). Following the general procedure outlined above, mesylate 30

(438 mg, 1.48 mmol) was processed to afford 36 (284 mg, 1.25 mmol, 84%). $^1$H NMR (D$_2$O) 4.40-4.36 (m, 1H), 3.66 (dd, J=12.3, 7.2 Hz, 1H), 3.48 (dd, J=12.8, 5.2 Hz, 1H), 3.26 (dd, J=12.8, 3.1 Hz, 1H), 3.21 (dd, J=12.2, 5.6 Hz, 1H), 2.76-2.70 (m, 1H), 2.62-2.50 (m, 4H), 1.61-1.51 (m, 2H), 1.40-1.33 (m, 2H), 0.86 (t, J=7.3 Hz, 3H). $^{13}$C NMR (D$_2$O) 73.5, 51.5, 48.6, 45.7, 32.2, 31.7, 31.3, 21.7, 13.3. HRMS (MH$^+$) calc for C$_9$H$_{20}$NOS: 190.1260. Found 190.1257.

Preparative Example 1.06

(3R,4S)-3-Hydroxy-4-(phenylthiomethyl)-pyrrolidine (37). Following the general procedure outlined above, mesylate 30 (300 mg, 1.00 mmol) was processed to afford 37 (692 mg, 0.69 mmol). $^1$H NMR (D$_2$O) 7.51-7.24 (m, 5H), 4.38-4.34 (m, 1H), 3.56 (dd, J=12.2, 7.7 Hz, 1H), 3.45 (dd, J=12.6, 5.2 Hz, 1H), 3.26-3.00 (m, 3H), 2.88 (dd, J=13.7, 8.3 Hz, 1H), 2.48-2.37 (m, 1H). $^{13}$C NMR (D$_2$O) 134.5, 130.5, 129.9, 127.6, 73.4, 51.5, 48.4, 45.5, 34.3.

Preparative Example 1.07

(3R,4S)-(4Fluorophenylthiomethyl)-3-hydroxypyrrolidine (38). Following the general procedure outlined above, mesylate 30 (281 mg, 0.951 mmol) was processed to afford 38 (160 mg, 0.607 mmol, 64%). $^1$H NMR (D$_2$O) 7.49-7.42 (m, 2H), 7.19-7.06 (m, 2H), 4.41-4.36 (m, 1H), 3.60 (dd, J=12.3, 7.7 Hz, 1H), 3.48 (dd, J=12.8, 5.2 Hz, 1H), 3.27-3.16 (m, 2H), 3.07 (dd, J=13.8, 6.9 Hz, 1H), 2.88 (dd, J=13.8, 8.3 Hz, 1H), 2.45-2.38 (m, 1H). $^{13}$C NMR (D$_2$O) 164.2, 160.9, 133.7, 133.6, 129.4, 116.9, 116.6, 73.3, 51.5, 48.4, 45.5, 35.5. HRMS (MH$^+$) calc for C$_{11}$H$_{15}$NOSF: 228.0853. Found 228.0856.

Preparative Example 1.08

(3R,4S)-(4-Chlorophenylthiomethyl)-3-hydroxy-4-pyrrolidine (39). Following the general procedure outlined above, mesylate 30 (245 mg, 0.83 mmol) was processed to afford 39 (212 mg, 0.76 mmol, 91%). $^1$H NMR (d$_4$-MeOH) 7.51-7.39 (m, 2H), 7.35-7.31 (m, 2H), 4.38-4.33 (m, 1H), 3.59 (dd, J=12.0, 7.6 Hz, 1H), 3.47 (dd, J=12.4, 4.9 Hz, 1H), 3.28-3.18 (m, 3H), 2.93 (dd, J=13.6, 9.0 Hz, 1H), 2.49-2.38 (m, 1H). $^{13}$C NMR (D$_2$O) 135.7, 134.1, 132.9, 130.8, 74.8, 52.9, 49.6, 47.5, 35.8.

Preparative Example 1.09

(3R,4S)-4-(3-Chlorophenylthiomethyl)-3-hydroxy-pyrrolidine (40). Following the general procedure outlined above, mesylate 30 (300 mg, 1.02 mmol) was processed to afford 40 (192 mg, 0.685 mmol, 67%). $^1$H NMR (D$_2$O) 7.33-7.15 (m, 4H), 4.39-4.35 (m, 1H), 3.59 (dd, J =12.2, 7.7 Hz, 1H), 3.47 (dd, J =12.7, 5.1 Hz, 1H), 3.28-3.04 (m, 3H), 2.89 (dd, J=13.7, 8.3 Hz, 1H), 2.49-2.41 (m, 1H). $^{13}$C NMR (D$_2$O) 136.9, 134.7, 131.0, 129.3, 128.1, 127.2, 73.4, 51.5, 48.4, 45.3, 34.0. HRMS (MH$^+$) calc for C$_{11}$H$_{15}$NOSCl: 244.0557(4). Found 244.0556(8).

Preparative Example 1.10

(3R,4S)-4-(Benzylthiomethyl)-3-hydroxy-pyrrolidine (41). Following the general procedure outlined above, mesylate 30 (1.10 g, 3.7 mmol) was processed to afford 41 (730 mg, 2.81 mmol, 76%). $^1$H NMR (D$_2$O) 7.40-7.27 (m, 5H), 4.26-4.22 (m, 1H), 3.74 (s, 2H), 3.56 (dd, J=12.4, 7.2 Hz, 1H), 3.37 (dd, J=12.8, 5.2 Hz, 1H), 3.21 (dd, J=12.8, 3.0 Hz, 3H), 2.07 (dd, J=12.4, 5.5 Hz, 1H), 2.61-2.52 (m, 1H), 2.47-2.34 (m, 2H). $^{13}$C NMR (D$_2$O) 138.7, 129.5, 129.3, 127.9, 73.5, 51.5, 48.5, 45.4, 35.9, 31.8. HRMS (MH$^+$) calc for C$_{12}$H$_{18}$NOS: 224.1109. Found 224.1102.

Preparative Example 1.11

(3R,4R)-3-Hydroxy-4-(methoxymethyl)-pyrrolidine (42), Scheme 4. The diol 29 was manipulated according to Scheme 4 to afford 42. $^1$H NMR (D$_2$O) 4.30-4.26 (m, 1H), 3.52-3.28 (m, 4H), 3.22 (s, 3H), 3.15-3.00 (m, 2H), 2.48-2.37 (m, 1H). $^{13}$C NMR (D$_2$O) 72.1, 71.6, 58.8, 52.0, 46.7, 45.7. HRMS (MH$^+$) calc for C$_6$H$_{14}$NO$_2$: 132.1019. Found 132.1012.

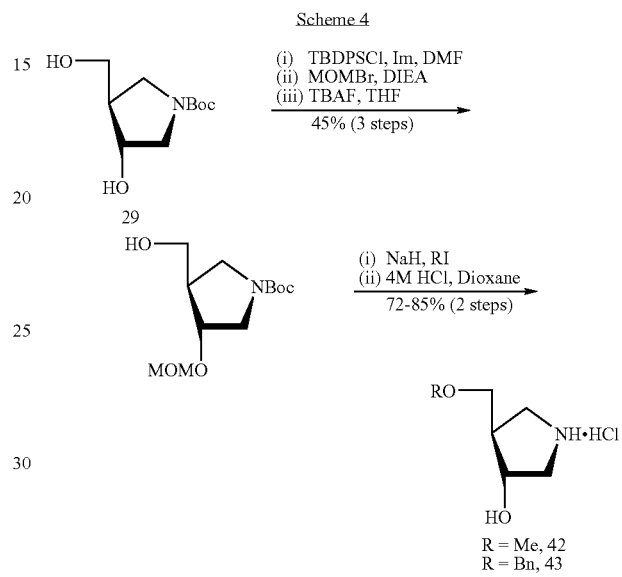

Scheme 4

Preparative Example 1.12

(3R,4R)-4-(Benzyloxymethyl)-3-hydroxy-pyrrolidine (43), Scheme 4. The diol 29 was manipulated according to Scheme 4 to afford 43. $^1$H NMR (D$_2$O, free base) 7.32-7.15 (m, 5H), 4.36 (s, 2H), 3.92-3.85 (m, 1H), 3.35 (dd, J=9.8, 7.0 Hz, 1H), 3.24 (dd, J=9.8, 7.8 Hz, 1H), 2.97 (dd, J=11.8, 7.9 Hz, 1H), 2.75 (dd, J=12.4, 5.5 Hz, 1H), 2.57 (dd, J=12.4, 3.4 Hz, 1H), 2.36 (dd, J=11.8, 5.7 Hz, 1H), 2.15-2.05 (m, 1H). $^{13}$C NMR (D$_2$O) 137.6, 129.0, 128.8, 128.6, 74.7, 73.1, 71.0, 53.2, 48.0, 47.6. HRMS (MH$^+$) calc for C$_{12}$H$_{18}$NO$_2$: 208.1332. Found 208.1329.

Preparative Example 1.13

(3R,4S)-4-(Cyclohexylthiomethyl)-3-hydroxy-pyrrolidine hydrochloride (44) To a solution of cyclohexylmercaptan (0.47 mL, 3.84 mmol) in DMF (10 mL) at 0° C. was added 60% NaH (145 mg, 3.6 mmol). After 10 min. of stirring, a solution of the mesylate 30 (565 mg, 1.91 mmol) in DMF (10 mL) was added. Stirring was continued while the reaction was allowed to attain r.t. After completion, the reaction was quenched with aq. NaHCO$_3$, toluene was added and the reaction was processed normally to give the crude intermediate which was subjected to column chromatography on silica eluting with petroleum ether: EtOAc (1:1 v/v) to give the clean intermediate (3R,4S)-N-tert-butoxycarbonyl-3-hydroxy-4-(cyclohexylthiomethyl)-pyrrolidine as a colourless syrup (428 mg, 71%). NMR (300 MHz, CDCl$_3$): δ ppm: 4.17-4.09 (m, 1H), 3.72-3.60 (m, 2H), 3.28-3.18 (m, 1H), 3.15-3.09 (m, 1H), 2.74-2.64 (m, 2H), 2.60-2.53 (m, 1H), 2.32-2.23 (m, 1H), 1.96 (m, 2H), 1.81-1.77 (m, 2H), 1.66-

1.61 (m, 1H), 1.45 (s, 9H), 1.35-1.24 (m, 5H). $^{13}$C NMR (300 MHz, CDCl$_3$): δ ppm: (note that some peaks are doubled due to slow conversion of rotamers) 154.91, 79.94, (75.57, 74.72), (52.80, 52.55), (49.70, 49.43), (46.24, 45.41), 44.26, 33.99, 33.93, 31.90, 28.87, 26.43, 26.12. A solution of this material in MeOH (10 mL) was treated with 12 N (conc.) HCl (4 mL) at 40° C. for 30 min. to give the crude title compound 44 which was used directly in a Mannich-type reaction.

Preparative Example 1.14

(3R,4S)-3-Hydroxy-4-(4-pyridylthiomethyl)-pyrrolidine (45). Following the general procedure outlined above, mesylate 30 (348 mg, 1.18 mmol) was processed to afford 45 (105 mg, 0.426 mmol, 36%). $^1$H NMR (D$_2$O) 8.42 (d, J=7.2 Hz, 2H), 7.82 (d, J=7.2 Hz, 2H), 4.51-4.46 (m, 1H), 3.74 (dd, J=12.4, 7.8 Hz, 1H), 3.57 (dd, J=12.8, 5.5 Hz, 1H), 3.44 (dd, J=13.6, 7.3 Hz, 1H) 3.34-3.22 (m, 3H), 2.78-2.60 (m, 1H). $^{13}$C NMR (D$_2$O) 164.1, 139.4, 122.9, 73.4, 51.4, 48.4, 44.3, 31.3. HRMS (MH$^+$) calc for C$_{10}$H$_{15}$N$_2$OS: 211.0900. Found 211.0908.

Preparative Example 2.01

(3R,4S)-3-Hydroxy-4-(2-phenylethyl)-pyrrolidine hydrochloride (49), Scheme 5. To a suspension of benzyltriphenylphosphonium bromide (1.75 g, 4.97 mmol) in dry THF (10 mL) under argon at 0° C. was added 1.6 M BuLi in THF (2.33 mL, 3.73 mmol) and the deep red solution left stirring without cooling for 10 min. After re-cooling to 0° C., the aldehyde 46 (335 mg, 1.56 mmol) [G. B. Evans, R. H. Fumeaux, A. Lewandowicz, V. L. Schramm, and P. C. Tyler, Second-Generation Transition State Analogues of Human Purine Nucleoside Phosphorylase, *J. Med. Chem.*, 46 (2003) 5271-5276] in THF (5 mL) was added and the mixture stirred at r.t. for 12 h. The reaction was then quenched with water (1 mL) and extracted with dichloromethane (100 mL). The organic phase was washed with sat. aq. NaHCO$_3$ (15 mL) then water (15 mL), dried (MgSO$_4$) and concentrated in vacuo. The residue was subjected to chromatography to afford a ca. 1:3 cis/trans mixture of (3R,4S)-N-tert-butoxycarbonyl-3-hydroxy-4-(2-phenylethenyl)-pyrrolidine (47) as a syrup (290 mg, 64%). $^1$H NMR (300 MHz, CDCl$_3$): δ ppm: trans: 7.28 (m, 5H), 6.49 (d, J=15.9 Hz, 1H), 6.03 (dd, J=15.9, 8.1 Hz, 1H), 4.11 (m, 1H), 3.67 (m, 2H), 3.32 (m, 2H), 2.83 (m, 1H), 1.46 (s, 9H); cis: 7.27 (m, 5H), 6.58 (d, J=11.6 Hz, 1H), 5.43 (dd, J=11.6 Hz, 10.0 Hz, 1H), 4.11 (m, 1H), 3.65 (m, 2H), 3.21 (m, 2H), 2.88 (m, 1H), 1.44 (s, 9H). To a solution of intermediate 47 (290 mg, 1.00 mmol) in ethanol (20 mL) was added 10% Pd/C (250 mg) and the suspension was stirred under an atmosphere of hydrogen for 12 h. After filtration, the solvent was removed in vacuo to give (3R,4S)-N-tert-butoxycarbonyl-3-hydroxy-4-(2-phenylethyl)pyrrolidine (48) as a syrup, 254 mg (87%). $^1$H NMR (300 MHz, CDCl$_3$): δ ppm: 7.10 (m, 5H), 4.00 (m, 1H), 3.47 (m, 2H), 3.07 (m, 2H), 2.67 (m, 2H), 2.04 (m, 1H), 1.83 (m, 1H), 1.54 (m, 1H), 1.45 (s, 9H). $^{13}$C NMR (300 MHz, CDCl$_3$): δ ppm (note that some peaks are doubled due to slow conversion of rotamers): 155.17, 142.03, 128.83, 128.71, 126.37, 79.88, (74.94, 71.26), (53.17, 52.90), (49.90, 49.34), (46.11, 45.52), 34.41, 33.69, 28.91. To a solution of intermediate 48 (254 mg, 0.87 mmol) in methanol (10 mL) was added 12N (conc.) HCl (4 mL) and the solution stirred at 40° C. for 30 min. After removal of the solvent in vacuo and azeotroping with toluene, the crude title compound (3R,4S)-3-Hydroxy-4-(2-phenylethyl)pyrrolidine hydrochloride 49 was obtained as a solid (202 mg, 0.89 mmol, 102%). $^1$H NMR (300 MHz, MeOH-d$_4$): δ ppm: 7.14 (m, 5H), 4.22 (m, 1H), 3.52 (dd, J=11.8, 7.4 Hz, 1H), 3.39 (dd, J=12.3, 4.9 Hz, 1H), 3.14 (dd, J=12.3, 2.8 Hz, 1H), 3.02 (dd, J=11.8 Hz, 1H), 2.71 (m, 2H), 2.20 (m, 1H), 1.84 (m, 1H), 1.62 (m, 1H). $^{13}$C NMR (300 MHz, MeOH-d$_4$): δ ppm: 142.94, 129.93, 129.89, 127.56, 75.56, 52.90, 48.55, 47.28, 35.18, 34.44.

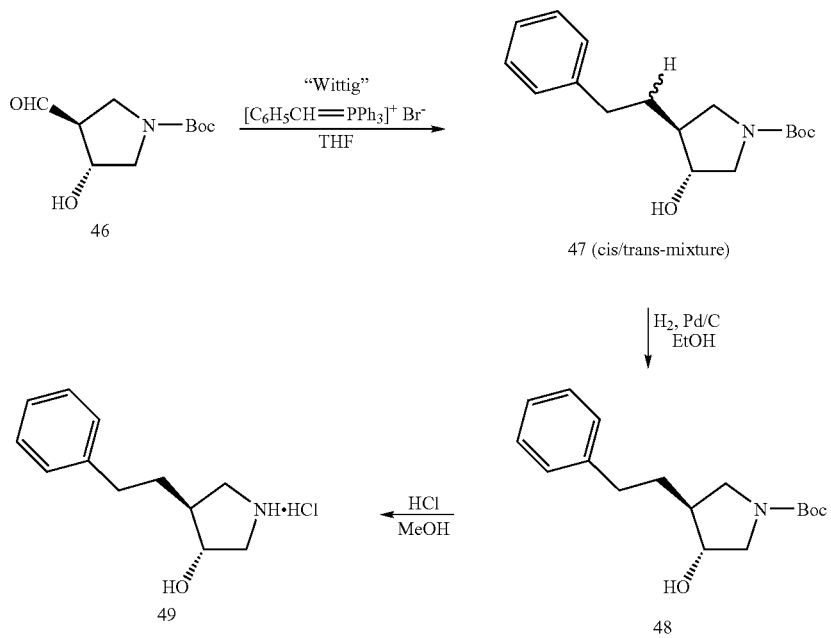

Scheme 5

Preparative Example 2.02

(3R,4S)-3-Hydroxy-4-propyl-pyrrolidine hydrochloride (52)

The synthesis of this compound follows the same general route outlined in scheme 5 [see Preparative Example 2.01]. To a suspension of ethyltriphenylphosphonium bromide (2.9 g, 6.93 mmol) in dry THF (15 mL) under argon at 0° C. was added 1.6 M BuLi in THF (4 mL, 6.40 mmol) and the deep red solution left stirring without cooling for 10 min. After re-cooling to 0° C., the aldehyde 46 (580 mg, 2.69 mmol) in THF (10 mL) was added and the mixture stirred at r.t. for 12 h. The reaction was then quenched with water (1 mL) and extracted with dichloromethane (100 mL). The organic phase was washed with sat. aq. $NaHCO_3$ (15 mL) then water (15 mL), dried over $MgSO_4$) and concentrated in vacuo. The residue was subjected to chromatography to afforded (3R,4S)-N-tert-butoxycarbonyl-3-hydroxy-4-propenyl-pyrrolidine (50) as a light yellow syrup (165 mg, 27%). To a solution of intermediate 50 (165 mg, 0.73 mmol) in ethanol (10 mL) was added 10% Pd/C (60 mg) and the suspension was stirred under an atmosphere of hydrogen for 3 h. After filtration, the solvent was removed in vacuo to give (3R,4S)-N-tert-butoxycarbonyl-3-hydroxy-4-propyl-pyrrolidine (51) as a syrup (172 mg, 102%). $^1$H NMR (300 MHz, $CDCl_3$): δ ppm: 3.98-3.96 (m, 1H), 3.61-3.57 (m, 3H), 3.22-3.18 (m, 1H), 3.10-3.01 (m, 1H), 2.03 (m, 1H), 1.45 (s, 9H), 1.41-1.31 (m, 2H), 1.24-1.12 (m, 1H), 0.94-0.89 (m, 3H). $^{13}$C NMR (300 MHz, $CDCl_3$): δ ppm (note that some peaks are doubled due to slow conversion of rotamers): 155.20, 79.69, (75.53, 74.76), (53.10, 52.80), (49.94, 49.38), (46.19, 45.67), 34.04, 28.83, 21.27, 14.47. To a solution of intermediate 51 (172 mg, 0.75 mmol) in methanol (10 mL) was added 12N (conc.) HCl (4 mL) and the solution stirred at 40° C. for 30 min. After removal of the solvent in vacuo and azeotroping with toluene, the crude title compound (3R,4S)-3-hydroxy-4-propyl-pyrrolidine hydrochloride (52) was obtained as a syrup (138 mg, 0.83 mmol, 111%). $^1$H NMR (300 MHz, MeOH-$d_4$): δ ppm: 4.20-4.16 (m, 1H), 3.59-3.52 (m, 1H), 3.44-3.39 (m, 1H), 3.19-3.14 (m, 1H), 3.05-2.99 (m, 1H), 2.23-2.17 (m, 1H), 1.55-1.28 (m, 4H), 0.98-0.94 (m, 3H). $^{13}$C NMR (300 MHz, MeOH-$d_4$): δ ppm: 75.65, 52.82, 50.30, 47.45, 34.69, 22.30, 14.78.

Preparative Example 3.01

9-Deaza-adenine. 6-Chloro-9-deazapurine (3 g, 19.5 mmol) was added to a saturated solution of ammonia in ethanol (30 mL). The resulting suspension was heated at 130° C. for 16 h in a sealed tube. The homogeneous solution was cooled, flash silica gel was added, and the suspension concentrated in vacuo. The resultant solid was loaded onto the top of a column of silica gel and eluted with methanol/$CH_2Cl_2$ (4:1 v/v) to afford 9-deaza-adenine as a pale yellow solid (2.16 g, 80%). $^{13}$C NMR ($d_4$-MeOH) δ ppm: 153.1, 149.9, 145.2, 131.3, 113.8, 101.6.

Preparative Example 4.01

(3R,4R)-3-Hydroxy-4-methanesulfonyloxy-pyrrolidine (53). A solution of HCl in 1,4-dioxane (4M, 2 mL) was added to a stirred solution of the mesylate 30 (169 mg, 0.572 mmol) in methanol (3 mL). After stirring at RT for 12 h, the solvents were removed in vacuo to give a residue to which methanol (×2) and then $D_2O$ was added and evaporated to give title compound 53 (120 mg, 0.518 mmol, 91%). $^1$H NMR ($D_2O$) 4.55-4.35 (m, 3H), 3.74 (dd, J=12.5, 8.4 Hz, 1H), 3.50 $^{13}$C NMR ($D_2O$) 71.3, 69.2, 52.0, 46.0, 45.3, 36.9. HRMS (MH$^+$) calc for $C_6H_4NO_4S$: 196.0638. Found 196.0648.

Although the invention has been described by way of example, it should be appreciated that variations or modifications may be made without departing from the scope of the invention. Furthermore, when known equivalents exist to specific features, such equivalents are incorporated as if specifically referred to in the specification.

INDUSTRIAL APPLICABILITY

The present invention provides a useful synthetic route to compounds that are inhibitors of PNP, PPRT, MTAN, MTAP and/or NH. The compounds may be useful in the treatment of diseases in which the inhibition of PNP, PPRT, MTAN, MTAP and/or NH is desirable. Such diseases include cancer, bacterial infection, protozoal infection or T-cell mediated diseases.

The invention claimed is:
1. A process for preparing a compound of the formula (I)

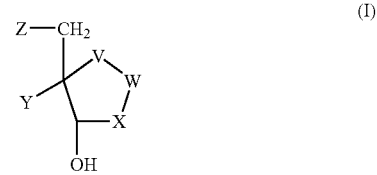

wherein:
V is selected from $CH_2$ and NH, and W is $NR^1$; or
V is $NR^1$, and W is selected from $CH_2$ and NH;
X is selected from $CH_2$ and CHOH in the R or S-configuration, except where W is selected from NH and $NR_1$, then X is $CH_2$;
Y is selected from hydrogen, halogen and hydroxy, except where V is selected from NH and $NR^1$, then Y is hydrogen;
Z is selected from hydrogen, halogen, hydroxy, a sulfonate leaving group, SQ, OQ and Q, where Q is an alkyl, aralkyl, or aryl group; and
$R^1$ is a radical of the formula (II)

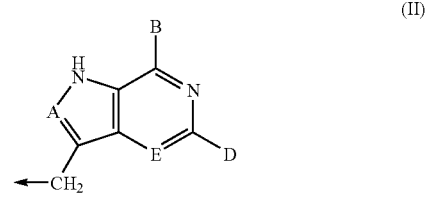

wherein:
A is selected from CH and $CR^2$, where $R^2$ is selected from halogen, alkyl, aralkyl, aryl, OH, $NH_2$, $NHR^3$, $NR^3R^4$ and $SR^5$, where $R^3$, $R^4$ and $R^5$ are each alkyl, aralkyl or aryl groups;
B is selected from OH, $NH_2$, $NHR^6$, SH, hydrogen and halogen, where $R^6$ is an alkyl, aralkyl or aryl group;
D is selected from OH, $NH_2$, $NHR^7$, hydrogen, halogen and $SCH_3$, where $R^7$ is an alkyl, aralkyl or aryl group; and
E is N;

including reacting a compound of the formula (III)

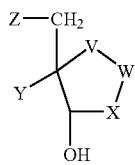

wherein:
V is selected from CH$_2$ and NH, and W is NH; or
V is NH, and W is selected from CH$_2$ and NH;
X is selected from CH$_2$ and CHOH in the R or S— configuration, except where W is NH, then X is CH$_2$;
Y is selected from hydrogen, halogen and hydroxy, except where V is selected from NH, then Y is hydrogen; and
Z is selected from hydrogen, halogen, hydroxy, a sulfonate leaving group, SQ, OQ and Q, where Q is an alkyl, aralkyl, or aryl group;
with a compound of the formula (IV)

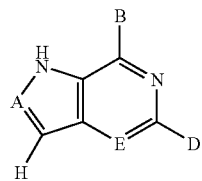

wherein A, B, D, and E are as defined above;
and with formaldehyde or a formaldehyde equivalent.

2. The process of claim 1, wherein Z is hydrogen, halogen, hydroxy, SQ or OQ, where Q is an alkyl, aralkyl or aryl group.

3. The process of claim 1, wherein A is CH.

4. The process of claim 1, wherein Y is H.

5. The process of claim 1, wherein W is NR$^1$, V is CH$_2$ and X is CH$_2$.

6. The process of claim 5, wherein R$^1$ is a radical of formula (II) where A is CH.

7. The process of claim 1, wherein D is H or NH$_2$.

8. The process of claim 1, wherein B is NH$_2$, OH or Cl.

9. The process of claim 1, wherein the sulfonate leaving group is methanesulfonyloxy, p-toluenesulfonyloxy or trifluoromethanesulfonyloxy.

10. The process of claim 9, wherein the sulfonate leaving group is methanesulfonyloxy.

11. The process of claim 1, wherein the compounds of formula (III) and (IV) are reacted with formaldehyde.

12. The process of claim 1, wherein the compounds of formula (III) and (IV) are reacted with a formaldehyde equivalent which is paraformaldehyde.

13. The process of claim 1, wherein the compound of formula (I) is:
(3R,4R)-1-[(9-deazahypoxanthin-9-yl)methyl]-3-hydroxy-4-hydroxymethyl-pyrrolidine;
(3R,4R)-1-[(9-deaza-adenin-9-yl)methyl]-3-hydroxy-4-(hydroxymethyl)-pyrrolidine;
(3R,4S)-4-(benzylthiomethyl)-1-[(9-deeza-adenin-9-yl)methyl]-3-hydroxy-pyrrolidine;
(3R,4R)-1-[(6-chloro-9-deazapurin-9-yl)methyl]-3-hydroxy-4-(hydroxymethyl)-pyrrolidine;
(3R,4R)-1-[(9-deaza-adenin-9-yl)methyl]-3-hydroxy-4-(methanesulfonyl)-pyrrolidine;
(3R,4S)-1-[(9-deaza-adenin-9-yl)methyl]-3-hydroxy-4-(methylthiomethyl)-pyrrolidine;
(3R,4S)-4-(ethylthiomethyl)-1-[(9-deaza-adenin-9-yl)methyl]-3-hydroxy-pyrrolidine;
(3R,4S)-1-[(9-deaza-adenin-9-yl)methyl]-3-hydroxy-4-(propylthiomethyl)-pyrrolidine;
(3R,4S)-1-[(9-deaza-adenin-9-yl)methyl]-3-hydroxy-4-(isopropylthiomethyl)-pyrrolidine;
(3R,4S)-4-(butylthiomethyl)-1-[(9-deaza-adenin-9-yl)methyl]-3-hydroxy-pyrrolidine;
(3R,4S)-1-[(9-deaza-adenin-9-yl)methyl]-3-hydroxy-4-(phenylthiomethyl)-pyrrolidine;
(3R,4R)-1-[(9-deaza-adenin-9-yl)methyl]-3-hydroxy-4-(methoxymethyl)-pyrrolidine;
(3R,4R)-4-(benzyloxymethyl)-1-[(9-deaza-adenin-9-yl)methyl]-3-hydroxy-pyrrolidine;
(3R,4R)-1-[(9-deazaguanin-9-yl)methyl]-3-hydroxy-4-hydroxymethyl-pyrrolidine;
(3R,4S)-1-(9-deazahypoxanthin-9-yl)-3-hydroxy-4-(propylthiomethyl)-pyrrolidine;
(3R,4S)-4-(butylthiomethyl)-1-[(9-deazahypoxanthin-9-yl)methyl]-3-hydroxy-pyrrolidine;
(3R,4S)-1-[(9-deaza-6-chloro-purin-9-yl)methyl]-3-hydroxy-4-(2-phenylethyl)pyrrolidine;
(3R,4S)-1-[(9-deazaadenin-9-yl)methyl]-3-hydroxy-4-propyl-pyrrolidine;
(3R,4S)-1-[(9-deazahypoxanthin-9-yl)methyl]-3-hydroxy-4-propyl pyrrolidine; or
(3R,4S)-1-[(9-deazahypoxanthin-9-yl)methyl]-3-hydroxy-4-(methylthiomethyl)-pyrrolidine.

14. A process for preparing a compound of the formula (I)

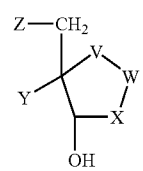

wherein:
V is selected from CH$_2$ and NH, and W is NR$^1$; or
V is NR$^1$, and W is selected from CH$_2$ and NH;
X is selected from CH$_2$ and CHOH in the R or S-configuration, except where W is selected from NH and NR$^1$, then X is CH$_2$;
Y is selected from hydrogen, halogen and hydroxy, except where V is selected from NH and NR$^1$, then Y is hydrogen;
Z is selected from hydrogen, halogen, hydroxy, a sulfonate leaving group, SQ, OQ and Q, where Q is an alkyl, aralkyl, or aryl group; and
R$^1$ is a radical of the formula (II)

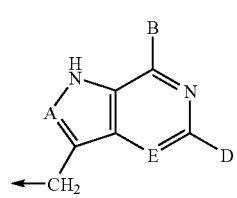

wherein:
- A is selected from CH and CR², where R² is selected from halogen, alkyl, aralkyl or aryl, OH, NH₂, NHR³, NR³R⁴ and SR⁵, where R³, R⁴ and R⁵ are each alkyl, aralkyl or aryl groups;
- B is selected from OH, NH₂, NHR⁶, SH, hydrogen and halogen, where R⁶ is an alkyl, aralkyl or aryl group;
- D is selected from OH, NH₂, NHR⁷, hydrogen, halogen and SCH₃, where R⁷ is an alkyl, aralkyl or aryl group; and
- E is N;

comprising
(i) reacting a compound of formula (III)

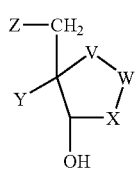
(III)

wherein:
- V is selected from CH₂ and NH, and W is NH; or
- V is NH, and W is selected from CH₂ and NH;
- X is selected from CH₂ and CHOH in the R or S-configuration, except where W is NH, then X is CH₂;
- Y is selected from hydrogen, halogen and hydroxy, except where V is selected from NH, then Y is hydrogen; and
- Z is selected from hydrogen, halogen, hydroxy, a sulfonate leaving group, SQ, OQ and Q, where Q is an alkyl, aralkyl, or aryl group;

with a compound of the formula (IV)

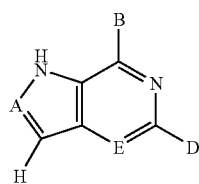
(IV)

wherein A, B, D, and E are as defined above;
and with formaldehyde or a formaldehyde equivalent,
where any one or more of V, W, X, Y and Z of the compound of formula (III) is protected with a protecting group and/or where any one or more of A, B, D and E of the compound of formula (IV) is protected with a protecting group; and
(ii) removing the one or more protecting groups to give the compound of formula (I).

15. The process of claim 14, where any one or more of V, W, X, Y and Z of the compound of formula (III) is protected with a protecting group.

16. The process of claim 14, where any one or more of A, B, D and E of the compound of formula (IV) is protected with a protecting group.

17. The process of claim 14, where any one or more of V, W, X, Y and Z of the compound of formula (III) is protected with a protecting group and where any one or more of A, B, D and E of the compound of formula (IV) is protected with a protecting group.

18. A process for preparing a compound of formula:

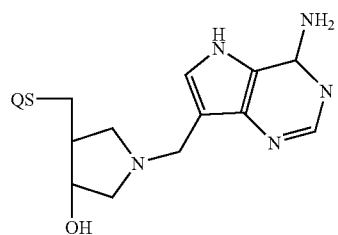

wherein Q is phenyl substituted with F or Cl, or wherein Q is cyclohexyl or pyridyl;
comprising reacting a compound of formula

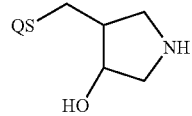

wherein Q is phenyl substituted with F or Cl, or wherein Q is cyclohexyl or pyridyl;
with a compound of formula

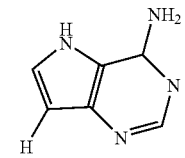

and with formaldehyde or a formaldehyde equivalent, wherein the compound is:
- (3R,4S)-4-(4-chlorophenylthiomethyl)-1-[(9-deaza-adenin-9-yl)methyl]-3-hydroxy-pyrrolidine,
- (3R,4S)-1-[(9-deaza-adenin-9-yl)methyl]-4-(4-fluorophenylthiomethyl)-3-hydroxy-pyrrolidine,
- (3R,4S)-4-(3-chlorophenylthiomethyl)-1-[(9-deaza-adenin-9-yl)methyl]-3-hydroxy-pyrrolidine,
- (3R,4S)-1-[(9-deaza-adenin-9-yl)methyl]-3-hydroxy-4-(cyclohexylthiomethyl) pyrrolidine, or
- (3R,4S)-1-[(9-deaza-adenin-9-yl)methyl]-3-hydroxy-4-(4-pyridylthiomethyl)-pyrrolidine.

\* \* \* \* \*

UNITED STATES PATENT AND TRADEMARK OFFICE
CERTIFICATE OF CORRECTION

PATENT NO. : 7,655,795 B2  Page 1 of 1
APPLICATION NO. : 10/543380
DATED : February 2, 2010
INVENTOR(S) : Evans et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 324 days.

Signed and Sealed this

Twenty-third Day of November, 2010

David J. Kappos
*Director of the United States Patent and Trademark Office*